US012366581B2

(12) United States Patent
Petropoulos et al.

(10) Patent No.: US 12,366,581 B2
(45) Date of Patent: Jul. 22, 2025

(54) METHODS, COMPOSITIONS, AND SYSTEMS FOR DETECTING CORONAVIRUS NEUTRALIZING ANTIBODIES

(71) Applicant: Laboratory Corporation of America Holdings, Burlington, NC (US)

(72) Inventors: Christos J. Petropoulos, Half Moon Bay, CA (US); Mary T. Wrin, Fremont, CA (US); Danielle DiTirro, Walnut Creek, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 887 days.

(21) Appl. No.: 17/359,064

(22) Filed: Jun. 25, 2021

(65) Prior Publication Data

US 2022/0065869 A1 Mar. 3, 2022

Related U.S. Application Data

(60) Provisional application No. 63/143,592, filed on Jan. 29, 2021, provisional application No. 63/126,164, filed on Dec. 16, 2020, provisional application No. 63/044,070, filed on Jun. 25, 2020.

(51) Int. Cl.

| | |
|---|---|
| ***C07K 16/10*** | (2006.01) |
| ***A61P 31/14*** | (2006.01) |
| ***C07K 14/005*** | (2006.01) |
| ***C07K 14/165*** | (2006.01) |
| ***C07K 16/28*** | (2006.01) |
| ***C12N 5/071*** | (2010.01) |
| ***C12N 9/02*** | (2006.01) |
| ***C12N 9/48*** | (2006.01) |
| ***C12N 9/64*** | (2006.01) |
| ***C12N 15/86*** | (2006.01) |
| ***G01N 33/50*** | (2006.01) |
| ***G01N 33/58*** | (2006.01) |
| ***G01N 33/68*** | (2006.01) |

(52) U.S. Cl.

CPC ....... *G01N 33/6854* (2013.01); *C07K 14/005* (2013.01); *C12N 5/0686* (2013.01); *C12N 9/0069* (2013.01); *C12N 9/485* (2013.01); *C12N 9/6424* (2013.01); *C12N 15/86* (2013.01); *G01N 33/5091* (2013.01); *G01N 33/581* (2013.01); *C12N 2740/16043* (2013.01); *C12N 2770/20022* (2013.01); *G01N 2333/165* (2013.01)

(58) Field of Classification Search

CPC .. A61K 39/215; A61K 39/12; C07K 16/1003; C07K 16/1002; C07K 14/165

See application file for complete search history.

(56) References Cited

PUBLICATIONS

CA Application No. 3,186,975 , "Office Action", Mar. 11, 2024, 5 pages.
EP Application No. 21745569.0 , "Office Action", Nov. 17, 2023, 4 pages.
International Application No. PCT/US2021/039185 , "International Preliminary Report on Patentability", Jan. 5, 2023, 8 pages.
Petropoulos, C. et al., "A Novel Phenotypic Drug Susceptibility Assay for Human Immunodeficiency Virus Type 1," Antimicrob. Agents Chemother. 44(4):920-928 (2000).
Richman, D. et al., "Rapid evolution of the neutralizing antibody response to HIV type 1 infection," PNAS 100(7):4144-4149 (2003).
Whitcomb, J. et al., "Development and Characterization of a Novel Single-Cycle Recombinant-Virus Assay to Determine Human Immunodeficiency Virus Type 1 Coreceptor Tropism," Antimicrob. Agents Chemother. 51(2):566-575 (2007).
Case, J. et al., "Neutralizing Antibody and Soluble ACE2 Inhibition of a Replication-Competent VSV-SARS-CoV-2 and a Clinical Isolate of SARS-CoV-2," Available Online at: https://www.biorxiv.org/content/10.1101/2020.05.18.102038v1.full.pdf, May 18, 2020, pp. 1-34.
Schmidt, F. et al., "Measuring SARS-CoV-2 Neutralizing Antibody Activity Using Pseudotyped and Chimeric Viruses", Available Online at: https://www.biorxiv.org/content/10.1101/2020.06.08.14087lv1.full.pdf, Jun. 9, 2020, pp. 1-34.
Vandergaast, R. et al., "Development and Validation of IMMUNO-COV™: A High-Throughput Clinical Assay for Detecting Antibodies that Neutralize SARS-CoV-2," Available Online at: https://www.biorxiv.org/content/10.1101/2020.05.26.117549vl.full.pdf, May 27, 2020, 32 pages.
Vandergaast, R. et al., "IMMUNO-COV v2.0: Development and Validation of a High-Throughput Clinical Assay for Measuring SARS-CoV-2-Neutralizing Antibody Titers," vol. 6, Issue 3. Available Online at: https://journals.asm.org/doi/pdf/10.1128/mSphere.00170-21, Jun. 2, 2021, pp. 1-21.
Zettl, F. et al., "Rapid Quantification of SARS-CoV-2-Neutralizing Antibodies Using Propagation-Defective Vesicular Stomatitis Virus Pseudotypes," Vaccines 8(3):386 (2020), 13 pages.
PCT/US2021/039185, International Search Report and Written Opinion, Sep. 24, 2021, 12 pages.
EP21745569.0, "Office Action," dated Aug. 9, 2024, 6 pages.

*Primary Examiner* — Barry A Chestnut
(74) *Attorney, Agent, or Firm* — Kilpatrick Townsend & Stockton LLP

(57) ABSTRACT

The present disclosure relates to methods, compositions, and systems for detecting whether a subject exposed to a coronavirus has developed a neutralizing antibody response. Also disclosed are methods for determining whether a patient infected by a coronavirus is likely to respond to treatment with an antibody preparation. Also disclosed are methods for detecting the level of neutralizing antibody response in a sample of serum from a subject exposed to a coronavirus or to a coronavirus vaccine.

17 Claims, 38 Drawing Sheets

Figure 4A - Anti-SARS CoV-2 nAb Titration Profiles
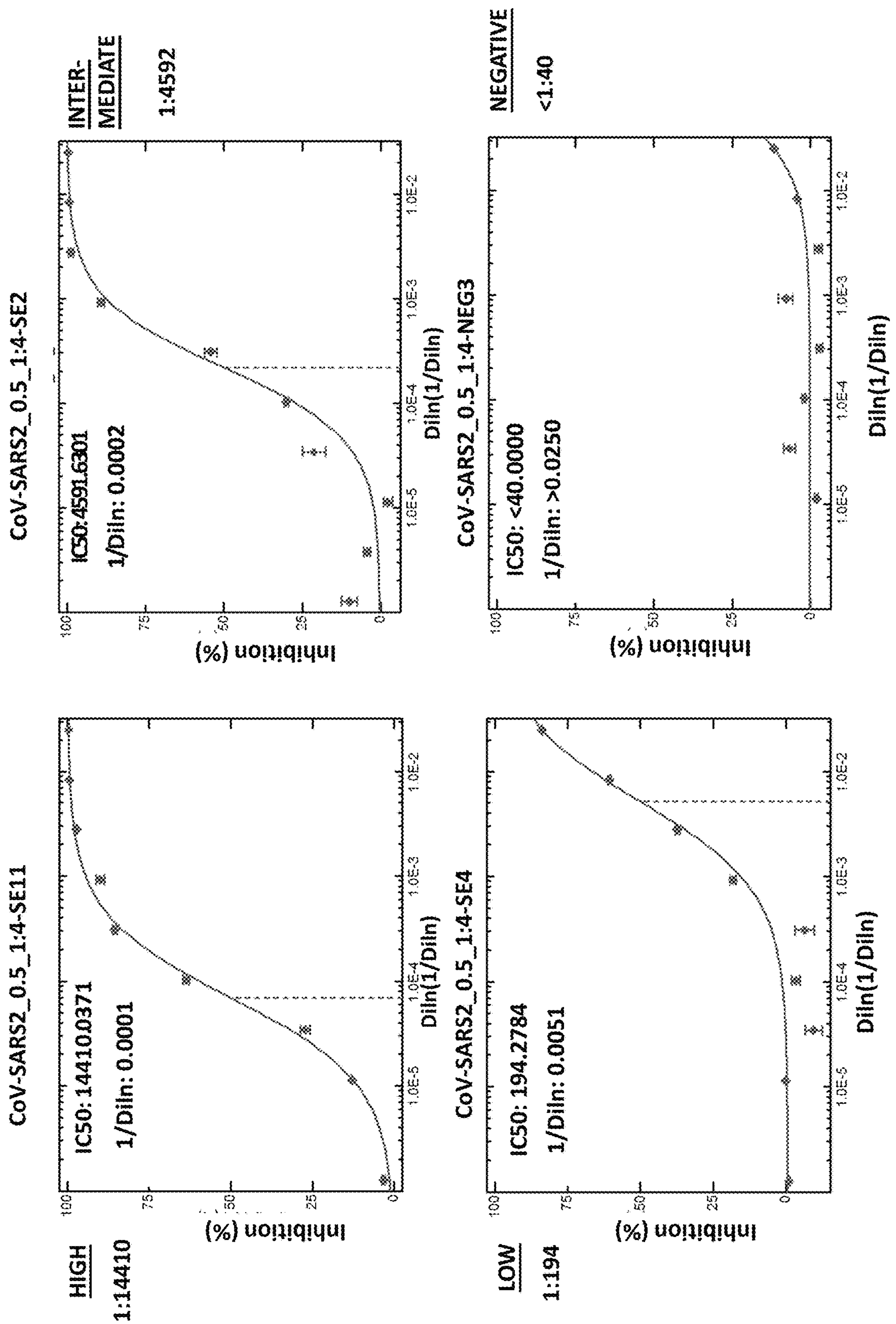

Figure 5A - Anti-SARS CoV-2 nAb Titers in Convalescent Sera
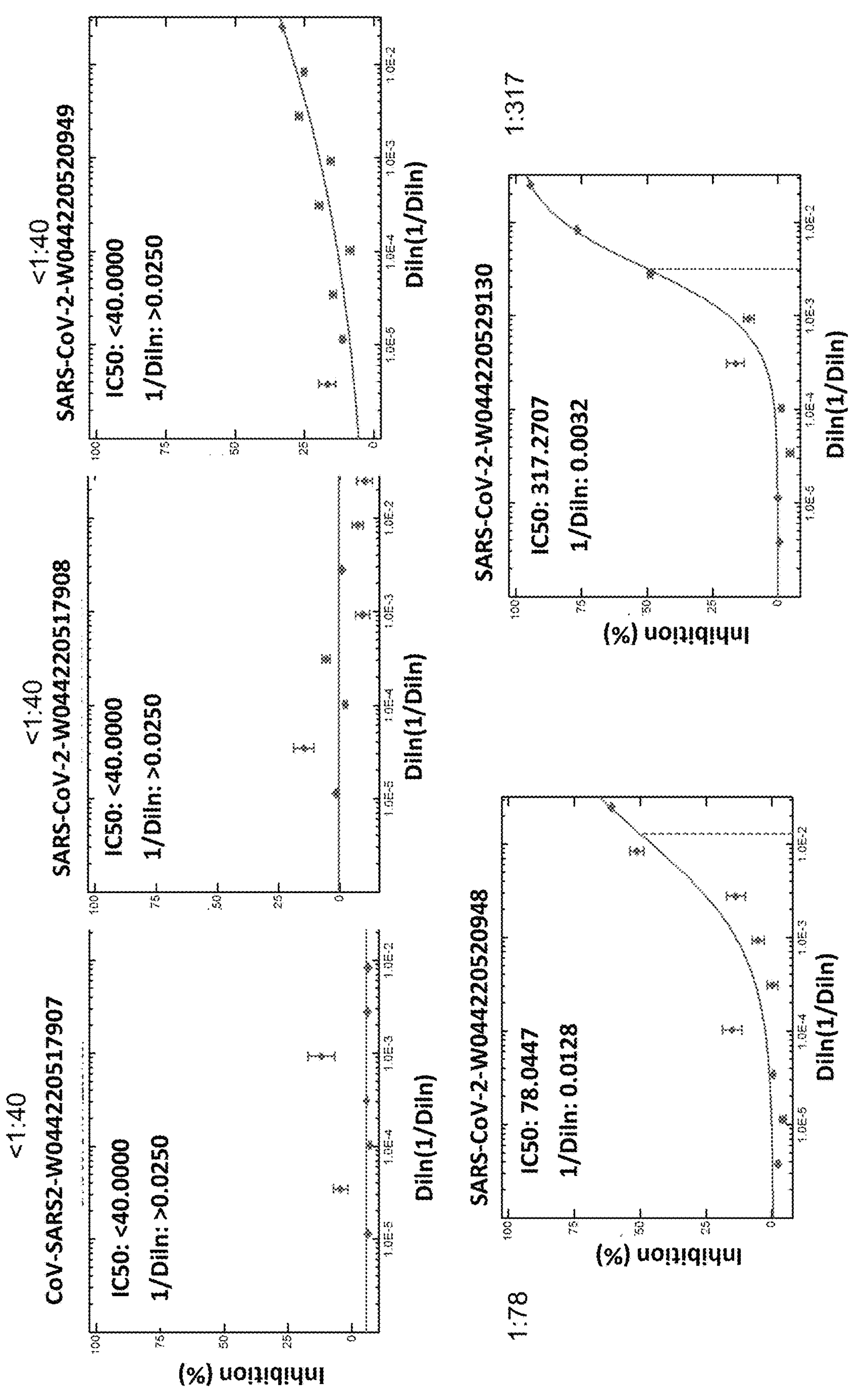

Anti-SARS CoV-2 nAb Titers in Convalescent Sera

Anti-SARS CoV-2 nAb Assay Reproducibility

Figure 8

Correlation of RBD Ab and S nAb

| Bar Code ID | Sample ID | anti-RBD Ab (ug/mL) | Ab status | Citrate Plasma vs Serum | nAb titer @ 50% inhibition of viral |
|---|---|---|---|---|---|
| W0442 205 20947 | Serum #1 | 44.8 | Positive | Equivalent | 1111, 1468 |
| | Plasma #1 | 39.5 | Positive | | 955 |
| W0442 205 20950 | Serum #2 | 50.7 | Positive | Equivalent | 1224, 1253 |
| | Plasma #2 | 45.6 | Positive | | 1,122 |
| W0442 205 29130 | Serum #3 | 32.6 | Positive | Equivalent | 317, 361 |
| | Plasma #3 | 32.8 | Positive | | 233 |
| W0442 205 20949 | Serum #4 | 15.9 | Borderline | Equivalent | <40, <40 |
| | Plasma #4 | 11.2 | Borderline | | <40 |
| W0442 205 20951 | Serum #5 | 45.2 | Positive | Equivalent | 1969, 1489 |
| | Plasma #5 | 41.1 | Positive | | 878 |
| W0442 205 17908 | Serum #6 | 5.1 | Negative | Equivalent | <40, <40 |
| | Plasma #6 | <1.0 | Negative | | <40 |
| W0442 205 17904 | Serum #7 | 44.3 | Positive | Equivalent | 2124, 2111 |
| | Plasma #7 | 43.9 | Positive | | 1,385 |
| W0442 205 17905 | Serum #8 | 66.6 | Positive | Equivalent | 413, 401 |
| | Plasma #8 | 68.7 | Positive | | 408 |
| W0442 205 20948 | Serum #9 | 9.7 | Borderline | Equivalent | 78, 104 |
| | Plasma #9 | 11.7 | Borderline | | 79 |
| W0442 205 17907 | Serum #10 | 7.3 | Negative | Equivalent | <40, <40 |
| | Plasma #10 | 5.8 | Negative | | <40 |

Correlation of RBD Ab and S nAb

Figure 10

Assay Accuracy and Inclusivity

| Assay Result (N = 131) | SARS CoV-2 nAb Positive | SARS CoV-2 nAb Negative |
|---|---|---|
| Serology/NAA Positive | 49/49 (100%) | 0/49 (0%) |
| Serology/NAA Negative | 1/50 (2%) | 49/50 (98%) |
| Historical Negative (2017 collection) | 0/32 (0%) | 32/32 (100%) |

Figure 11

Intra-Assay Precision (Manual Serum Dilution, Transient ACE2 Expression)

| Precision Sample | High Titer Positive | Intermediate Titer Positive | Low Titer Positive | Negative |
|---|---|---|---|---|
| **$ID_{50}$ Mean** | **54,710** | **6,643** | **1,089** | **<40** |
| $ID_{50}$ Median | 47,802 | 6,153 | 937 | <40 |
| $ID_{50}$ Maximum | 89,947 | 10,732 | 1,636 | <40 |
| $ID_{50}$ Minimum | 39,983 | 4,658 | 836 | <40 |
| **$ID_{50}$ Variation (Max/Min)** | **2.2** | **2.3** | **2.0** | **1** |
| $ID_{50}$ Std. Dev. | 18,722 | 2,260 | 312 | NA |
| $ID_{50}$ CV (%) | 34.2 | 34 | 28.6 | NA |
| Replicate Number | 6 | 6 | 6 | 6 |

Figure 12

Intra-Assay Precision (Manual Serum Dilution, Stable ACE2 Expression)

| Precision Sample | High Titer Positive | Intermediate Titer Positive | Low Titer Positive | Negative |
|---|---|---|---|---|
| **$ID_{50}$ Mean** | **25,980** | **2,550** | **575** | **<40** |
| $ID_{50}$ Median | 24,839 | 2,527 | 590 | <40 |
| $ID_{50}$ Maximum | 36,694 | 3,337 | 748 | <40 |
| $ID_{50}$ Minimum | 14,629* | 1,874 | 425 | <40 |
| **$ID_{50}$ Variation (Max/Min)** | **2.5** | **1.8** | **1.8** | **1** |
| $ID_{50}$ Std. Dev. | 8,684 | 671 | 117 | NA |
| $ID_{50}$ CV (%) | 33.4 | 26.3 | 20.3 | NA |
| Replicate Number | 6 | 6 | 6 | 6 |

Figure 13

Intra-Assay Precision (Automated Serum Dilution, Transient ACE2 Expression)

| Precision Sample | High Titer Positive | Intermediate Titer Positive | Low Titer Positive | Negative |
|---|---|---|---|---|
| **$ID_{50}$ Mean** | **27,770** | **3,455** | **773** | **<40** |
| $ID_{50}$ Median | 28,097 | 3,503 | 789 | <40 |
| $ID_{50}$ Maximum | 41,933 | 4,551 | 893 | <40 |
| $ID_{50}$ Minimum | 18,899 | 2,599 | 679 | <40 |
| **$ID_{50}$ Variation (Max/Min)** | **2.2** | **1.8** | **1.3** | **1** |
| $ID_{50}$ Std. Dev. | 8,161 | 719 | 82.8 | NA |
| $ID_{50}$ CV (%) | 29.4 | 20.8 | 10.7 | NA |
| Replicate Number | 6 | 6 | 6 | 6 |

Figure 14

Intra-Assay Precision (Automated Serum Dilution, Stable ACE2 Expression)

| Precision Sample | High Titer Positive | Intermediate Titer Positive | Low Titer Positive | Negative |
|---|---|---|---|---|
| **$ID_{50}$ Mean** | **37,817** | **2,935** | **736** | **<40** |
| $ID_{50}$ Median | 37,822 | 3,029 | 748 | <40 |
| $ID_{50}$ Maximum | 52,042 | 3,669 | 890 | <40 |
| $ID_{50}$ Minimum | 20,127 | 1,522 | 586 | <40 |
| **$ID_{50}$ Variation (Max/Min)** | **2.6** | **2.4** | **1.5** | **1** |
| $ID_{50}$ Std. Dev. | 13,041 | 756 | 121 | NA |
| $ID_{50}$ CV (%) | 34.5 | 25.7 | 16.4 | NA |
| Replicate Number | 6 | 6 | 6 | 6 |

Figure 15

Inter-Assay Precision

| Precision Sample | High Titer Positive | Intermediate Titer Positive | Low Titer Positive | Negative |
|---|---|---|---|---|
| **$ID_{50}$ Mean** | **36,569** | **3,896** | **793** | **<40** |
| $ID_{50}$ Median | 32,794 | 3,195 | 754 | <40 |
| $ID_{50}$ Maximum | 54,710 | 6,643 | 1,089 | <40 |
| $ID_{50}$ Minimum | 25,980 | 2,550 | 575 | <40 |
| **$ID_{50}$ Variation (Max/Min)** | **2.1** | **2.6** | **1.9** | **1** |
| $ID_{50}$ Std. Dev. | 16,844 | 2,208 | 272 | <40 |
| $ID_{50}$ CV (%) | 48.4 | 56.7 | 34.3 | <40 |
| Assay Run Number | 4 | 4 | 4 | 4 |

Figure 16

Inter-Assay Precision: Manual vs. Automated Serum Dilution

| Precision Sample | M:A Ratio High Titer Positive | M:A Ratio Intermed. Titer Positive | M:A Ratio Low Titer Positive | M:A Ratio Negative Titer |
|---|---|---|---|---|
| **$ID_{50}$ Mean** | **1.3** | **1.4** | **1.1** | **1** |
| $ID_{50}$ Median | 1.4 | 1.2 | 1 | 1 |
| $ID_{50}$ Maximum | 1.7 | 2.4 | 1.8 | 1 |
| $ID_{50}$ Minimum | 0.8 | 1.2 | 0.7 | 1 |

M:A Ratio: Manual Value (Runs A, B) ÷ Automated Value (Runs C, D)

Figure 17

Inter-Assay Precision: Transient vs. Stable ACE2 Expression

| Precision Sample | M:A Ratio High Titer Positive | M:A Ratio Intermed. Titer Positive | M:A Ratio Low Titer Positive | M:A Ratio Negative Titer |
|---|---|---|---|---|
| **$ID_{50}$ Mean** | **1.3** | **1.8** | **1.4** | **1** |
| $ID_{50}$ Median | 1.3 | 1.6 | 1.4 | 1 |
| $ID_{50}$ Maximum | 1.7 | 2.9 | 1.8 | 1 |
| $ID_{50}$ Minimum | 1.3 | 1.7 | 1.6 | 1 |

T:S Ratio: Transient ACE2 Value (Runs A, C) ÷ Stable ACE2 Value (Runs B, D)

Figure 18

Assay Linearity

| Sample ID 215168 | High Titer Serum | Diluted 1:3 | Diluted 1:9 | Diluted 1:27 | Diluted 1:81 | Diluted 1:243 |
|---|---|---|---|---|---|---|
| Nominal $ID_{50}$ | (22,224) | 7,408 | 2,469 | 823 | 274 | 91 |
| Observed $ID_{50}$ | 22,224 | 6,746 | 1,667 | 670 | 178 | 87 |
| Predicted $ID_{50}$ | NA | 7,408 | 2,249 | 556 | 223 | 59 |
| N:O Ratio | NA | 1.1 | 1.5 | 1.2 | 1.5 | 1.0 |
| **O:P Ratio** | **NA** | **0.9** | **0.7** | **1.2** | **0.8** | **1.5** |

N:O Ratio: Nominal Value ÷ Observed Value
O:P Ratio: Observed Value ÷ Predicted Value
The Predicted Value is calculated as a three-fold dilution based on the preceding observed $ID_{50}$ value.

Figure 20

Assay Reactivity: Immunoglobulin Depletion

| Reactivity Sample | Low Titer Serum 1 W044220529130 | Low Titer Serum 2 215387 | Negative Titer Serum W044220517907 |
|---|---|---|---|
| LTS $ID_{50}$ | 231 | 551 | <40 |
| LTS + Protein G $ID_{50}$ | 66 | 289 | <40 |
| **Fold Depletion** | **3.5** | **1.9** | **NA** |

Figure 21

Assay Reactivity: % Inhibition at Serial Dilutions Pre- and Post-Immunoglobulin Depletion

| Sample ID | 1:40 | 1:120 | 1:360 | 1:1080 | 1:3240 | 1:9720 | 1:29160 |
|---|---|---|---|---|---|---|---|
| LTS-1 | **99.1%** | **70.4%** | **36.0%** | 21.6% | -1.0% | 7.3% | -0.9% |
| LTS-1 + Protein G | **62.6%** | **36.7%** | **8.0%** | 8.0% | 8.6% | 7.4% | -5.1% |
| LTS-2 | **97.8%** | **92.8%** | **62.6%** | 22.9% | 29.4% | 8.2% | 11.4% |
| LTS-2 + Protein G | **89.0%** | **65.3%** | **52.9%** | 19.4% | 6.1% | 9.5% | - |
| NTS | 11.6% | 5.9% | 0.9% | 15.8% | -1.0% | -2.1% | -10.0% |
| NTS + Protein G | -4.0% | -12.2% | -7.5% | -12.7% | -11.4% | 1.5% | 9.9% |

Figure 22

Cross Reactivity: Pre-SARS CoV-2 Pandemic Sera (Historic Negative Samples)

| Precision Sample | Anti-SARS CoV-2 (N=32) | | Anti-SARS CoV (N=32) | |
|---|---|---|---|---|
| | POS | NEG | POS | NEG |
| **Number** | **0/32 (0%)** | **32/32 (100%)** | **15/32 (47%)** | **17/32 (53%)** |
| $ID_{50}$ Mean | NA | <40 | 61 | <40 |
| $ID_{50}$ Median | NA | <40 | 53 | <40 |
| $ID_{50}$ Maximum | NA | <40 | 103 | 75* |
| $ID_{50}$ Minimum | NA | <40 | 43 | <40 |
| **$ID_{50}$ Variation (Max/Min)** | **NA** | **NA** | **2.4** | **NA** |
| $ID_{50}$ Std. Dev. | NA | NA | 17 | NA |
| $ID_{50}$ CV (%) | NA | NA | 33 | NA |

NA: not applicable

* A single SARS CoV sample with a titer >40 was not called POS because the titer (75) was not 3-fold higher than the corresponding titer of the Specificity Control.

Figure 23

Cross Reactivity/Selectivity: Anti-viral Antibodies

| Anti-viral Antibody | Historic Negative Sample Number | Neutralizing Antibody Positive | |
|---|---|---|---|
| | | Anti-SARS CoV-2 | Anti-SARS CoV |
| Anti-viral Ab Vehicle (PBS) | 4 | 0/4 | 2/4 |
| Anti-HIV-1 Antibody | 4 | 0/4 | 2/4 |
| Anti-HBV Antibody | 4 | 0/4 | 2/4 |
| Anti-HCV Antibody | 4 | 0/4 | 2/4 |
| Anti-SARS CoV Antibody | 4 | 0/4 | 2/4 |

Vehicle: Phosphate Buffered Saline
Antiviral Antibody Concentration: 200 µg/mL

Figure 24

Interference Testing: Endogenous Components

| Interfering Substance | Anti-SARS CoV-2 nAb Titer ($ID_{50}$) | | | |
|---|---|---|---|---|
| | HTS 215168 | ITS 215204 | LTS 215204 | NTS 215204 |
| Sample Alone | 24,129 | 5,548 | 809 | <40 |
| Plus Vehicle (DMSO) | 36,439 | 2,361 | 865 | <40 |
| Plus Hemoglobin | 39,271 | 4,749 | 569 | <40 |
| Plus Bilirubin | 51,646 | 3,098 | 927 | <40 |
| Plus Triglyceride | 43,634 | 3,405 | 698 | <40 |
| Plus Albumin | 41,249 | 4,091 | 675 | <40 |
| Mean | 39,395 | 3,876 | 757 | <40 |

Vehicle: DMSO; dimethyl sulfoxide
Hemoglobin: 1% lysed blood
Bilirubin final concentration 20 μg/mL
Triglyceride final concentration: 2.5 mg/mL
Albumin final concentration: 50 mg/mL

Figure 25

Interference Testing: Specimen Type

| Sample Type Comparison | Sample Number | Paired Sample Assay Results | | | |
|---|---|---|---|---|---|
| | | POS/POS | POS/NEG | NEG/POS | NEG/NEG |
| Serum: ACD plasma | 20 | 12/20 (60%) | 3/20 (15%) | 1/20 (5%) | 4/20 (20%) |
| ACD plasma : EDTA plasma | 4 | 2/4 (50%) | 0/4 (0%) | 0/4 (0%) | 2/4 (50%) |
| ACD plasma : Heparin plasma | 5 | 5/5 (100%) | 0/5 (0%) | 0/5 (0%) | 0/5 (0%) |

ACD: acid-citrate-dextrose; EDTA: ethylene-diamine-tetra-acetic acid.

Figure 26

Assay Sensitivity

| SARS CoV-2 nAb Low Titer Sample | Operator | No. Replicates | Titer Mean | Titer Range | Titer > 1:40 | Titer < 1:40 |
|---|---|---|---|---|---|---|
| W044220520948 (undiluted) | 1 | 3 | 95 | 84-102 | 3/3 (100%) | 0/3 (0%) |
| W044220520948 (diluted 1:2) | 1 | 3 | 56 | 48-72 | 3/3 (100%) | 0/3 (0%) |
| W044220520948 (diluted 1:3) | 1 | 3 | <40 | <40 | 0/3 (0%) | 3/3 (100%) |
| W044220520948 (undiluted) | 2 | 3 | 82 | 69-102 | 3/3 (100%) | 0/3 (0%) |
| W044220520948 (diluted 1:2) | 2 | 3 | <46 | <40-49 | 2/3 (67%) | 1/3 (33%) |
| W044220520948 (diluted 1:3) | 2 | 3 | <40 | <40 | 0/3 (0%) | 3/3 (100%) |

Figure 27

Sample Stability

| Sample Handling Storage Condition | Handling Storage Time | Low Titer Serum | | Intermediate Titer Serum | |
|---|---|---|---|---|---|
| | | Rep1/Rep2 | Max:Min | Rep1/Rep2 | Max:Min |
| Time 0 | Time 0 | 185/208 | 1.12 | 1,866/2,443 | 1.31 |
| Ambient ( 20° - 30° C) | 48 hour (+/- 4 hr) | 195/201 | 1.03 | 1,493/1,947 | 1.30 |
| Refrigerated (4° - 8°C) | 48 hour (+/- 4 hr) | 212/256 | 1.21 | 1,730/1,384 | 1.25 |
| Frozen (< -15° C) | ≥ 14 day | 156/180 | 1.15 | 1,689/1,775 | 1.05 |
| 5X Freeze/Thaw | NA | 274/185 | 1.48 | 2,066/1,826 | 1.13 |
| **Mean** | **NA** | **204/206** | **1.01** | **1,769/1,875** | **1.06** |

NA: not applicable

Figure 28

In-Process Assay Reagent Stability

| Critical Reagent Lot | Storage Handling Storage | SARS CoV-2 | | Specificity Control | |
|---|---|---|---|---|---|
| | | Hour 0 Rep1/Rep2 | ~Hour 6 Rep1/Rep2 | Hour 0 Rep1/Rep2 | ~Hour 6 Rep1/Rep 2 |
| LTS CR Lot 1 | Ambient | 247/156 | 206/172 | 43/52 | <40/51 |
| LTS CR Lot 2 | Ambient | 211/161 | 250/181 | 41/<40 | <40/42 |
| LTS CR Lot 1* | Refrigerated | 177/ - | 235/ - | 47/<40 | 247/<40 |
| LTS CR Lot 2 | Refrigerated | 263/225 | 205/326 | <40/42 | 41/<40 |
| LTS CR Lot 1 | Frozen | 156/214 | 241/284 | <40/<40 | <40/60 |
| LTS CR Lot 2 | Frozen | 180/179 | 213/240 | <40/<40 | <40/43 |
| **Mean** | **NA** | **205/187** | **225/241** | **<40/<40** | **<40/<40** |
| ITS CR Lot 1 | Ambient | 1,121/1,556 | 1,863/1,880 | <40/<40 | <40/<40 |
| ITS CR Lot 2 | Ambient | 1,801/1,597 | 3,372/1,390 | <40/<40 | <40/<40 |
| ITS CR Lot 1* | Refrigerated | 1,542/1,395 | 1,721/1,339 | <40/<40 | <40/<40 |
| ITS CR Lot 2 | Refrigerated | 1,466/1,959 | 1,378/1,929 | <40/<40 | <40/<40 |
| ITS CR Lot 1 | Frozen | 1,689/1,008 | 1,731/2,369 | <40/64 | <40/<40 |
| ITS CR Lot 2 | Frozen | 1,775/1,521 | 1,425/1,307 | <40/<40 | <40/<40 |
| **Mean** | **NA** | **1,566/1,253** | **1,915/1,702** | **<40/<40** | **<40/<40** |

5x freeze/thaw conditions were not evaluated for CR; CR are prepared and stored as single-use aliquots.
*SARA CoV-2 pseudovirus was not added to sample replicate 2 due to operator error. The specificity control for sample replicate 1 for this sample was high.

Error bars = SEM. Averaged data from 4 independent days.

Error bars = SEM. Averaged data from 4 independent days.

Figure 32

| SARS-CoV-2 Variant | Single mutation | AVERAGERLU fold difference from Wuhan | STDEV |
|---|---|---|---|
| Wuhan | | 1 | 0 |
| D614G | | 2.9 | 0.8 |
| | | | |
| B.1.1.7 | | 3.5 | 0.9 |
| B.1.1.7 | DEL69-70 | 2.9 | 0.6 |
| B.1.1.7 | DEL145 | 3.1 | 1.2 |
| B.1.1.7 | *N501Y | 2.1 | 0.6 |
| B.1.1.7 | A570D | 2.4 | 0.8 |
| B.1.1.7 | P681H | 2.9 | 0.6 |
| B.1.1.7 | T716I | 0.8 | 0.3 |
| B.1.1.7 | S982A | 2.9 | 1.1 |
| B.1.1.7 | D1118H | 1.8 | 0.5 |
| | | | |
| B.1.351 | | 1.8 | 1.2 |
| B.1.351 | D80A | 2.4 | 1.2 |
| B.1.351 | D215G | 5.5 | 1.7 |
| B.1.351 | DEL242-244 | 1.1 | 0.2 |
| B.1.351 | R426I | 0.7 | 0.2 |
| B.1.351 | K417N | 4.2 | 1.6 |
| B.1.351 | *E484K | 1.5 | 0.3 |
| B.1.351 | *N501Y | 2.1 | 0.6 |
| B.1.351 | A701V | 2.3 | 0.7 |
| | | | |
| B.1.1.28.1 | | 2.1 | 1.1 |
| B.1.1.28.1 | L18F | 1.6 | 0.7 |
| B.1.1.28.1 | T20N | 1.7 | 0.5 |
| B.1.1.28.1 | P26S | 1.9 | 0.6 |
| B.1.1.28.1 | D138Y | 1.4 | 0.8 |
| B.1.1.28.1 | R190S | 1.9 | 0.8 |
| B.1.1.28.1 | K417T | 3.5 | 1.4 |
| B.1.1.28.1 | *E484K | 1.5 | 0.3 |
| B.1.1.28.1 | *N501Y | 2.1 | 0.6 |
| B.1.1.28.1 | H655Y | 3.8 | 1.2 |
| B.1.1.28.1 | T1027I | 1.8 | 0.6 |
| B.1.1.28.1 | V1176F | 1.6 | 0.6 |
| | | | |
| B.1.417/429 | | 1.9 | 0.5 |
| B.1.427/429 | S13I | 1.3 | 0.4 |
| B.1.427/429 | W152C | 1.4 | 0.6 |
| B.1.427/429 | L452R | 2.8 | 1.1 |

Figure 33

| | Specificity Control Virus | SARS-CoV-2 PsV D614G | SARS-CoV-2 PsV B.1.1.7 | SARS-CoV-2 PsV DEL69-70 | SARS-CoV-2 PsV N501Y | SARS-CoV-2 PsV A570D | SARS-CoV-2 PsV T716I | SARS-CoV-2 PsV S982A | SARS-CoV-2 PsV D1118H |
|---|---|---|---|---|---|---|---|---|---|
| Sera Pool 001 | <40 | 45,314 | 8,473 | 41,754 | 20,135 | 44,121 | 20,320 | 28,430 | 26,535 |
| Sera Pool 002 | <40 | 48,663 | 22,211 | 35,558 | 23,981 | 22,845 | 11,202 | 21,018 | 14,598 |
| Sera Pool 003 | <40 | 10,070 | 3,679 | 12,378 | 5,954 | 11,847 | 6,023 | 10,702 | 6,550 |
| Sera Pool 004 | <40 | 12,573 | 2,040 | 18,072 | 12,983 | 15,057 | 9,890 | 13,940 | 6,737 |
| Sera Pool 005 | <40 | 8,891 | 2,166 | 8,219 | 9,087 | 9,999 | 4,742 | 8,535 | 7,981 |
| Sera Pool 006 | <40 | 5,941 | 710 | 8,236 | 3,222 | 6,455 | 3,127 | 5,947 | 3,534 |
| Sera Pool 007 | <40 | 4,092 | 851 | 5,934 | 2,567 | 3,945 | 2,646 | 3,239 | 2,918 |
| Sera Pool 008 | <40 | 2,600 | 2,162 | 4,222 | 3,235 | 1,833 | 1,966 | 4,687 | 2,850 |
| Sera Pool 009 | <40 | 3,348 | 55,347 | 5,069 | 4,702 | 6,299 | 2,367 | 3,253 | 3,275 |
| Sera Pool 010 | <40 | 2,012 | 1,874 | 3,377 | 2,893 | 6,692 | 1,811 | 1,591 | 2,280 |
| Sera Pool 011 | <40 | 4,118 | 1,073 | 5,668 | 3,744 | 5,182 | 3,351 | 3,243 | 3,489 |
| Sera Pool 012 | <40 | 1,211 | 385 | 3,150 | 1,575 | 2,689 | 1,267 | 2,165 | 1,313 |

Figure 34

| | SARS-CoV-2 PsV D614G | SARS-CoV-2 PsV B.1.1.7 | SARS-CoV-2 PsV DEL69-70 | SARS-CoV-2 PsV N501Y | SARS-CoV-2 PsV A570D | SARS-CoV-2 PsV T716I | SARS-CoV-2 PsV S982A | SARS-CoV-2 PsV D1118H |
|---|---|---|---|---|---|---|---|---|
| Sera Pool 001 | 1.00 | 0.19 | 0.92 | 0.44 | 0.97 | 0.45 | 0.63 | 0.56 |
| Sera Pool 002 | 1.00 | 0.48 | 0.76 | 0.51 | 0.49 | 0.24 | 0.45 | 0.31 |
| Sera Pool 003 | 1.00 | 0.37 | 1.23 | 0.59 | 1.16 | 0.60 | 1.06 | 0.65 |
| Sera Pool 004 | 1.00 | 0.16 | 1.44 | 1.03 | 1.20 | 0.79 | 1.11 | 0.54 |
| Sera Pool 005 | 1.00 | 0.24 | 0.92 | 1.02 | 1.12 | 0.53 | 0.96 | 0.90 |
| Sera Pool 006 | 1.00 | 0.12 | 1.39 | 0.54 | 1.09 | 0.53 | 1.00 | 0.59 |
| Sera Pool 007 | 1.00 | 0.21 | 1.45 | 0.63 | 0.96 | 0.65 | 0.79 | 0.71 |
| Sera Pool 008 | 1.00 | 0.83 | 1.62 | 1.24 | 0.71 | 0.76 | 1.60 | 1.10 |
| Sera Pool 009 | 1.00 | N/A | 1.51 | 1.40 | 1.88 | 0.71 | 0.97 | 0.98 |
| Sera Pool 010 | 1.00 | 0.93 | 1.68 | 1.44 | 3.33 | 0.90 | 0.79 | 1.13 |
| Sera Pool 011 | 1.00 | 0.26 | 1.38 | 0.91 | 1.26 | 0.81 | 0.79 | 0.85 |
| Sera Pool 012 | 1.00 | 0.38 | 1.30 | 0.89 | 1.29 | 0.63 | 0.94 | 0.76 |
| MEAN | | 0.38 | 1.30 | 0.89 | 1.29 | 0.63 | 0.94 | 0.76 |
| MEDIAN | | 0.26 | 1.38 | 0.90 | 1.14 | 0.64 | 0.95 | 0.74 |

METHODS, COMPOSITIONS, AND SYSTEMS FOR DETECTING CORONAVIRUS NEUTRALIZING ANTIBODIES

RELATED APPLICATIONS

This application claims priority to U.S. Provisional Application No. 63/044,070, filed Jun. 25, 2020, U.S. Provisional Application No. 63/126,164, filed Dec. 16, 2020 and U.S. Provisional Application No. 63/143,592, filed Jan. 29, 2021. The disclosures of U.S. Provisional Application Nos. 63/044,070, 63/126,164 and 63/143,592 are incorporated by reference herein in their entireties.

FIELD

The present disclosure relates to the detection of virus-neutralizing antibodies.

BACKGROUND

There is a need in the art for an assay that accurately assesses a subject's immune response to a virus such as SARS CoV-2. The 2019/2020 SARS CoV-2 outbreak in Wuhan China has provided sobering evidence that regional outbreaks of zoonotic virus infection have the potential to spread rapidly across much larger geographic regions. Given the widespread distribution of infections, SARS CoV-2 may now be established as an endemic virus in the world population.

Although the development of effective antiviral agents that rapidly suppress SARS CoV-2 virus replication will be invaluable in the therapeutic control of ongoing and/or future outbreaks, a preventative vaccine is currently viewed as the most effective approach to reducing the risk of future SARS CoV-2 outbreaks, epidemics, and pandemics. Literally hundreds of immunization strategies are being explored to develop safe and effective SARS CoV-2 vaccines. Many of the most promising approaches are designed to elicit broadly protective humoral immune responses resulting in neutralizing antibody (nAb) activity directed at the coronavirus spike protein.

Until such time that SARS CoV-2 infection can be effectively treated with existing and novel antiviral medications and/or immunotherapies, clinical treatment options for the severely ill will likely include treatment with convalescent sera/plasma donated by individuals that recently recovered from SARS CoV-2 infection.

However, the correlates of SARS CoV-2 protective immunity and therapeutic efficacy are unknown. Protection from virus infection, or suppression of virus replication may involve various components of the innate and adaptive immune systems. Evidence is emerging to indicate that B-cell mediated humoral immune responses (i.e., neutralizing antibodies) may be critical for protection and viral clearance. Currently there is an intense and comprehensive effort to develop, validate, and implement diagnostic assays to reliably characterize antibody responses to SARS CoV-2 infection and immunization.

The pathogenicity of SARS CoV-2 necessitates that all cell-based in vitro studies involving live (i.e. replication competent) virus are performed under BSL3 containment, including assessments of nAb activity. The assay as disclosed herein provides an accurate, reproducible, and high-throughput alternative that can be conducted under BSL2 containment resulting in reduced risk to laboratory personnel and lower costs to vaccine sponsors and providers of convalescent sera.

Such an assay allows for studies to establish protective immunity levels to SARS CoV-2 and would contribute to predicting individual prognoses and monitoring recovery following an infection with the pathogen. Additionally, the assay can be used to study vaccine and treatment responses and to assist in the selection of donor plasma for convalescent plasma therapy. Presently available assays are insufficient for these applications.

SUMMARY

It is an object of the present disclosure to provide methods for detecting coronavirus neutralizing antibodies. The methods may be embodied in a variety of ways.

In some embodiments, the present disclosure provides a method for detecting whether a subject exposed to a coronavirus has developed a neutralizing antibody response, comprising (a) transfecting into a plurality of first cells: i) a nucleic acid encoding a coronavirus spike protein, and ii) a viral expression vector which comprises an indicator nucleic acid which produces a detectable signal; (b) incubating the first cells under conditions such that the first cells produce viral particles comprising the coronavirus spike protein; (c) contacting the viral particles of step (b) with a second cell in the presence or absence of a sample comprising an antibody from the subject, wherein the second cell expresses a cell surface receptor to which the coronavirus binds; (d) measuring the amount of the detectable signal produced by the second cell in order to determine the infectivity of the viral particles in the presence or absence of the sample; and (e) comparing the amount of signal measured in step (d) in the presence of the sample with the amount of signal produced in step (d) in the absence of the sample, wherein a reduced amount of signal measured in the presence of the sample indicates that the subject has developed a neutralizing antibody response capable of reducing infection.

In other embodiments, the present disclosure provides a method for determining whether a first subject infected by a virus is likely to respond to treatment with an antibody preparation, comprising: (a) transfecting into a plurality of first cells: i) a nucleic acid encoding a coronavirus spike protein from the subject, and ii) a viral expression vector which comprises an indicator nucleic acid which produces a detectable signal; (b) incubating the first cells under conditions such that the first cells produce viral particles comprising the coronavirus spike protein; (c) contacting the viral particles of step (b) with a second cell in the presence or absence of an antibody preparation, wherein the second cell expresses a cell surface receptor to which the virus binds; (d) measuring the amount of the detectable signal produced by the second cell in order to determine the infectivity of the viral particles in the presence or absence of the antibody preparation; and (e) comparing the amount of signal measured in step (d) in the presence of the antibody preparation with the amount of signal produced in step (d) in the absence of the antibody preparation, wherein a reduced amount of signal measured in the presence of the antibody preparation indicates that the subject is likely to be responsive to treatment with the antibody preparation.

In other embodiments, the present disclosure provides a method for detecting the level (i.e., titer) of neutralizing antibody response in a sample from a subject exposed to a coronavirus or to a coronavirus vaccine, comprising: (a) transfecting into a plurality of first cells: i) a nucleic acid encoding a coronavirus spike protein, and ii) an viral expression vector which comprises an indicator nucleic acid which produces a detectable signal; (b) incubating the first cells under conditions such that the first cells produce viral particles comprising the coronavirus spike protein; (c) contacting the viral particles of step (b) with a second cell in the presence or absence of a sample from the subject that was exposed to a coronavirus or to a coronavirus vaccine, wherein the second cell expresses a cell surface receptor to which the coronavirus binds; (d) measuring the amount of the detectable signal produced by the second cell in order to determine the infectivity of the viral particles in the presence or absence of the sample; and (e) comparing the amount of signal measured in step (d) in the presence of the sample with the amount of signal produced in step (d) in the absence of the sample, and; (f) determining the level of a neutralizing antibody response in the sample based on the extent of the reduction in infectivity of the viral particles exposed to the sample as compared to the infectivity of the viral particles not exposed to the sample.

In other embodiments, the present disclosure provides methods to evaluate the effect of a mutation in a SARS CoV-2 spike protein on susceptibility to an anti-SARS CoV-2 neutralizing antibody. For example, the method may comprise (a) transfecting into a first portion of a plurality of first cells: i) a nucleic acid encoding a control coronavirus spike protein, and ii) a viral expression vector which comprises an indicator nucleic acid which produces a detectable signal; and (b) transfecting into a second portion of a plurality of first cells: i) a nucleic acid encoding a coronavirus spike protein that comprises a mutation and ii) a viral expression vector which comprises an indicator nucleic acid which produces a detectable signal. The method may then further comprise (c) incubating the first and second portion of first cells separately under conditions such that the first portion cells produce first viral particles comprising the control coronavirus spike protein, and the second portion cells produce second viral particles comprising the coronavirus spike protein having the mutation. The method may further comprise (d) contacting the first viral particles of step (c) with a first portion of a plurality of second cells in the presence of a sample comprising an antibody that binds SARS CoV-2 (i.e., an anti-SARS CoV-2 antibody), wherein the second cell expresses a cell surface receptor to which the coronavirus binds. The method may further comprise (e) contacting the second viral particles of step (c) with a second portion of a plurality of second cells in the presence of the sample comprising an antibody that binds SARS CoV-2, wherein the second cell expresses a cell surface receptor to which the coronavirus binds. The method may further comprise (f) measuring the amount of the detectable signal produced by the second cell in steps (d) and (e), wherein a reduced amount of signal produced by the second cell in step (d) as compared to the signal produced by the second cell in step (e) indicates that the mutation in the spike protein confers a reduced susceptibility of the viral particles to the anti-SARS CoV-2 antibody.

Also disclosed are compositions for the detection of a compound such as a neutralizing antibody that can modulate SARS infectivity. In certain embodiments, the composition may comprise cells that have been engineered to be either producer cells or target cells as disclosed herein. For example, the system may comprise a first cell (or cells) that has been genetically modified to be a target cell that expresses an angiotensin-converting enzyme 2 receptor (ACE-2). In some embodiments, the target cell may be genetically modified to also express human airway transmembrane trypsin-like serine protease (TMPRSS2). In some embodiments, and as discussed herein, the ACE2 and/or TMPRSS2 may be introduced into the target cell in a manner that allows for transient expression. Or, the ACE2 and/or TMPRSS2 may be introduced into the target cell in a manner that allows for stable expression. Also, disclosed are genetic constructs for making producer and/or target cells.

Also disclosed are kits, systems, and computer-program products tangibly embodied in a non-transitory machine-readable storage medium, including instructions configured to perform any of the steps of the methods or run any part of the systems.

BRIEF DESCRIPTION OF THE DRAWINGS

FIG. 4A and FIG. 4B depict examples of anti-SARS CoV-2 nAb titration profiles generated in accordance with an embodiment of the disclosure where the x-axis shows the dilution of the subject's sera as 1/Dilution (e.g., 1/100 dilution=1.0E-2, and the y-axis shows percent inhibition. The dilution which resulted in 50% inhibition for each of the serum samples tested is indicated above each graph.

FIG. 5A and FIG. 5B depict examples of anti-SARS CoV-2 nAb titration profiles in convalescent sera generated in accordance with an embodiment of the disclosure, where the x-axis shows the dilution of the subject's sera as 1/Dilution (e.g., 1/100 dilution=1.0E-2, and the y-axis shows percent inhibition. The dilution which resulted in 50% inhibition for each of the serum samples tested is indicated above each graph.

FIG. 8 depicts a table correlating results of anti-SARS CoV-2 receptor binding domain assays and anti-SARS CoV-2 nAb titers generated for both serum and plasma using an embodiment of the assay disclosed herein.

FIG. 10 depicts a table of assay accuracy and inclusivity test results generated from an embodiment of the assay disclosed herein.

FIG. 11 depicts a table of intra-assay precision results when the assay is conducted using manual serum dilutions and cells transiently expressing ACE-2 in accordance with an embodiment of the disclosure.

FIG. 12 depicts a table of intra-assay precision results when the assay is conducted using manual serum dilutions and cells stably expressing ACE-2 in accordance with an embodiment of the disclosure.

FIG. 13 depicts a table of intra-assay precision results when the assay is conducted using automated serum dilutions and cells transiently expressing ACE-2 in accordance with an embodiment of the disclosure.

FIG. 14 depicts a table of intra-assay precision results when the assay is conducted using automated serum dilutions and cells stably expressing ACE-2 in accordance with an embodiment of the disclosure.

FIG. 15 depicts a table of inter-assay precision results generated from embodiments of the assay using high titer, intermediate titer, low titer, and negative control samples.

FIG. 16 depicts a table of inter-assay precision results generated from comparing embodiments of the assay using either manual or automated serum dilutions.

FIG. 17 depicts a table of inter-assay precision results generated from comparing embodiments of the assay using either cells transiently expressing ACE-2 or stably expressing ACE-2.

FIG. 18 depicts a table of assay linearity results generated from an embodiment of the assay run with samples at five different three-fold dilutions.

FIG. 20 details the reactivity of an embodiment of the assay in samples that have undergone immunoglobulin depletion.

FIG. 21 details the reactivity of an embodiment of the assay in samples that have undergone immunoglobulin depletion and are serially diluted.

FIG. 22 details cross-reactivity testing of an embodiment of the assay using historically negative samples and testing for anti-SARS CoV-2 and anti-SARS CoV neutralizing antibodies.

FIG. 23 details cross-reactivity testing for an embodiment of the assay using negative serum samples spiked with concentrations of antibodies directed to HIV, HBV, HCV, and SARS CoV.

FIG. 24 details the results of interference testing done carried out using samples containing interfering substances in an embodiment of the assay.

FIG. 25 details the results of interference testing done using an embodiment of the assay to compare serum, plasma collected with acid citrate dextrose (ACD), plasma collected with EDTA, and plasma collected with heparin.

FIG. 26 shows the results of sensitivity testing done using an embodiment of the assay to compare calculated titers of undiluted, diluted 1:2 and diluted 1:3 low titer SARS CoV2 nAB samples.

FIG. 27 details the results of sample stability testing carried out using an embodiment of the assay disclosed herein.

FIG. 28 details the results of assay reagent stability testing carried out using an embodiment of the assay disclosed herein.

FIG. 32 shows the calculated infectivity (relative luminescence units; RLU) for each of a number of tested variants and single mutant pseudoviruses in accordance with an embodiment of the disclosure.

FIG. 33 shows an example (B1.1.7) ID50 table displaying neutralization titers for each sample generated from a 10-point sample titration curve in accordance with an embodiment of the disclosure.

FIG. 34 shows the fold difference of each sample (B.1.1.7) titer for each pseudovirus normalized using D614G SARS-CoV-2 pseudovirus, along with mean and median in accordance with an embodiment of the disclosure.

DETAILED DESCRIPTION

Figure 1:
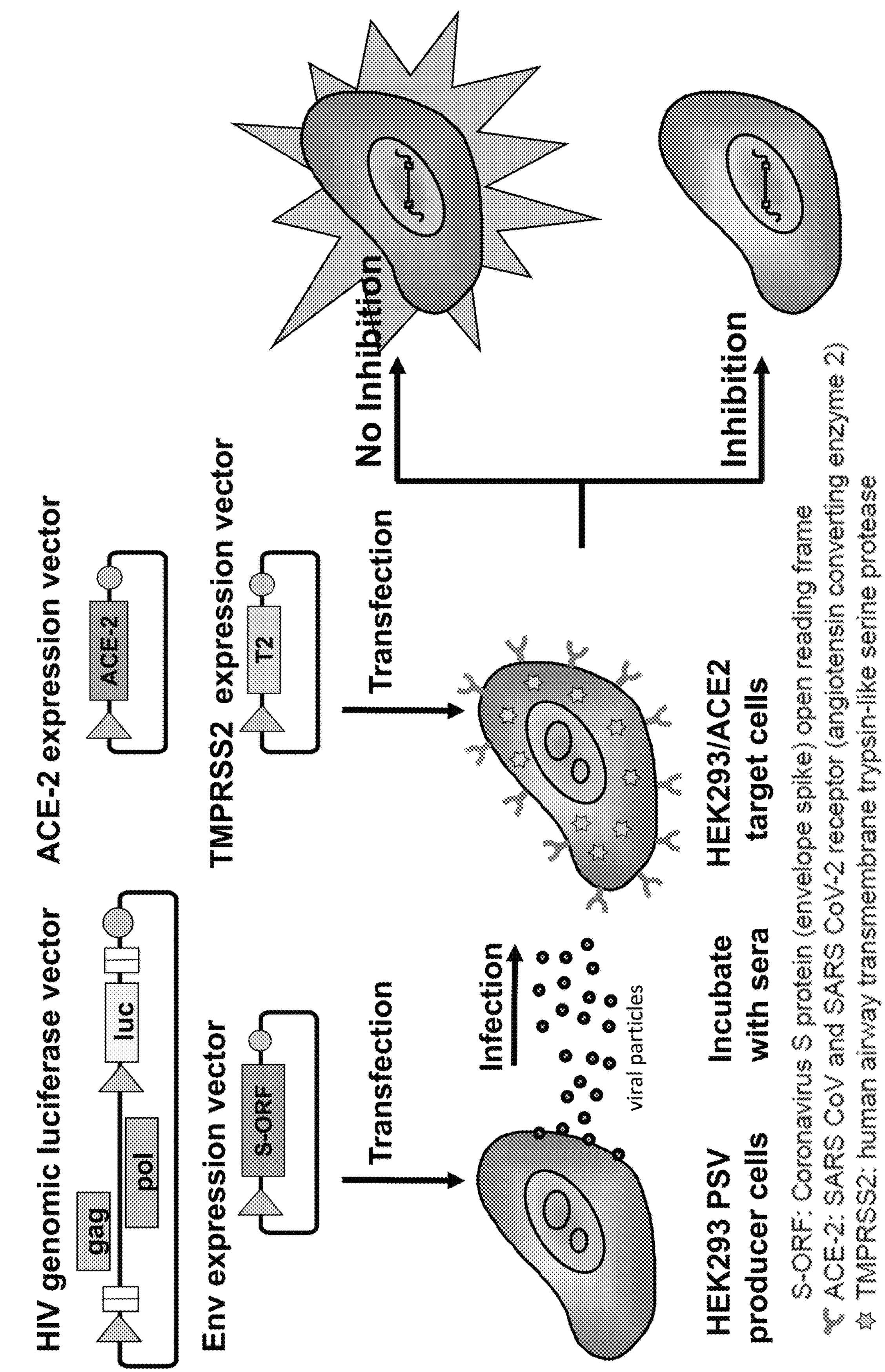
FIG. 1 depicts an example assay to detect coronavirus neutralizing antibodies in accordance with an embodiment of the disclosure wherein angiotensin converting enzyme 2 (ACE-2) and human airway transmembrane trypsin-like serine protease (TMPRSS2) are transiently expressed in target cells. PSV refers to pseudovirus; S-ORF refers to the Coronavirus S protein (envelope spike protein) open reading frame; and luc refers to luciferase. Pseudovirions are shown as viral particles emanating from producer cells. Fluorescence of the target cells (indicating a lack of inhibition of infection by the sera) is shown as color emanating from the target cells.

The following description recites various aspects and embodiments of the present compositions and methods. No particular embodiment is intended to define the scope of the compositions and methods. Rather, the embodiments merely provide non-limiting examples of various methods and systems that are at least included within the scope of the compositions and methods. The description is to be read from the perspective of one of ordinary skill in the art; therefore, information well known to the skilled artisan is not necessarily included.

Definitions

The present disclosure now will be described more fully hereinafter. The disclosure may be embodied in many different forms and should not be construed as limited to the aspects set forth herein; rather, these aspects are provided so that this disclosure will satisfy applicable legal requirements. Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

When introducing elements of the present disclosure or the embodiment(s) thereof, the articles "a," "an," "the," and "said" are intended to mean that there are one or more of the elements. The terms "comprising," "including," and "having" are intended to be inclusive and mean that there may be additional elements other than the listed elements. It is understood that aspects and embodiments of the disclosure described herein include "consisting" and/or "consisting essentially of" aspects and embodiments.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B, and/or C" is intended to mean A alone, B alone, C alone, A and B in combination, A and C in combination, B and C in combination, or A, B, and C in combination.

Various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

"Sample" or "patient sample" or "biological sample" or "specimen" are used interchangeably herein. The source of the sample may be solid tissue as from a fresh tissue, frozen and/or preserved organ or tissue or biopsy or aspirate. The source of the sample may be a liquid sample. Non-limiting examples of liquid samples include cell-free nucleic acid, blood or a blood product (e.g., serum, plasma, or the like), urine, nasal swabs, biopsy sample (e.g., liquid biopsy for the detection of cancer) or combinations thereof. The term "blood" encompasses whole blood, blood product, or any fraction of blood, such as serum, plasma, buffy coat, or the like as conventionally defined. Suitable samples include those which are capable of being deposited onto a substrate for collection and drying including, but not limited to: blood, plasma, serum, urine, saliva, tear, cerebrospinal fluid, organ, hair, muscle, or other tissue sampler other liquid aspirate. In an embodiment, the sample body fluid may be separated on the substrate prior to drying. For example, blood may be deposited onto a sampling paper substrate which limits migration of red blood cells allowing for separation of the blood plasma fraction prior to drying in order to produce a dried plasma sample for analysis. For example, in certain embodiments (e.g., COVID-19) the biological sample comprises a specimen from either the upper or lower respiratory system. In an embodiment, the sample may comprise e.g., at least one of a nasopharyngeal swab, a mid-turbinate swab, anterior nares swab, an oropharyngeal swab, sputum, a lower respiratory tract aspirate, a bronchoalveolar lavage, a nasopharyngeal wash and/or aspirate, or a nasal aspirate. The sample may contain compounds that are not naturally intermixed with the tissue in nature such as preservatives, anticoagulants, buffers, fixatives, nutrients, antibiotics, or the like.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, or sheep) and a primate (e.g., a monkey, such as a cynomolgus monkey, gorilla, chimpanzee, or a human).

As used herein, the terms "pseudovirus," "pseudovirion," and "viral particles" may be used interchangeably.

"Treatment," and other forms of this word refer to the administration of an agent to impede a disease. Treatment may also refer to any course which one skilled, for example, a treating physician, deems expedient.

As used herein, the term "titer" refers to the concentration of an analyte of interest. As used herein, "titer" may refer to the concentration of an antibody. In some embodiments, "titer" may refer to the concentration of a neutralizing antibody, such as a neutralizing antibody that recognized the Sars-CoV-2 spike protein.

Methods

In some embodiments, the present disclosure provides a method for detecting whether a subject exposed to a coronavirus has developed a neutralizing antibody response, comprising (a) transfecting into a plurality of first cells: i) a nucleic acid encoding a coronavirus spike protein, and ii) a viral expression vector which comprises an indicator nucleic acid which produces a detectable signal; (b) incubating the first cells under conditions such that the first cells produce viral particles comprising the coronavirus spike protein; (c) contacting the viral particles of step (b) with a second cell in the presence or absence of a sample comprising an antibody from the subject, wherein the second cell expresses a cell surface receptor to which the coronavirus binds; (d) measuring the amount of the detectable signal produced by the second cell in order to determine the infectivity of the viral particles in the presence or absence of the sample; and (e) comparing the amount of signal measured in step (d) in the presence of the sample with the amount of signal produced in step (d) in the absence of the sample, wherein a reduced amount of signal measured in the presence of the sample indicates that the subject has developed a neutralizing antibody response capable of reducing infection.

In other embodiments, the present disclosure provides for a method for determining whether a subject infected by a virus is likely to respond to treatment with an antibody preparation, comprising: (a) transfecting into a plurality of first cells: i) a nucleic acid encoding a coronavirus spike protein from the subject, and ii) a viral expression vector which comprises an indicator nucleic acid which produces a detectable signal; (b) incubating the first cells under conditions such that the first cells produce viral particles comprising the coronavirus spike protein from the subject; (c) contacting the viral particles of step (b) with a second cell in the presence or absence of the antibody preparation, wherein the second cell expresses a cell surface receptor to which the virus binds; (d) measuring the amount of the detectable signal produced by the second cell in the presence or absence of the antibody preparation; and (e) comparing the amount of signal measured in step (d) in the presence of the antibody preparation with the amount of signal produced in step (d) in the absence of the antibody preparation, wherein a reduced amount of signal measured in the presence of the antibody preparation from the second subject indicates that the subject is likely to be responsive to treatment with the antibody preparation. In certain embodiments, the antibody preparation is convalescent sera from a second subject.

In other embodiments, the present disclosure provides a method for detecting the level (e.g., titer) of neutralizing antibody response in a sample from subject exposed to a coronavirus comprising: (a) transfecting into a plurality of first cells: i) a nucleic acid encoding a coronavirus spike protein, and ii) a viral expression vector which comprises an indicator nucleic acid which produces a detectable signal; (b) incubating the first cells under conditions such that the first cells produce viral particles comprising the coronavirus spike protein; (c) contacting the viral particles of step (b) with a second cell in the presence or absence of the sample from the subject that was exposed to a coronavirus, wherein the second cell expresses a cell surface receptor to which the coronavirus binds; (d) measuring the amount of the detectable signal produced by the second cell in order to determine the infectivity of the viral particles in the presence or absence of the sample; and (e) comparing the amount of signal measured in step (d) in the presence of the sample with the amount of signal produced in step (d) in the absence of the sample, and; (f) determining the level of a neutralizing antibody response in the sample based on the extent of the reduction in infectivity of the viral particles exposed to the sample as compared to the infectivity of the viral particles not exposed to the sample. In some embodiments, the sample is a serum sample. In an embodiment, the measured level of neutralizing antibody is correlated to the World Health Organization International Standard having a defined level of International Units (IU) per milliliter (mL).

In other embodiments, the present disclosure provides a method for detecting the level of neutralizing antibody response (e.g., titer) in a sample from subject exposed to a coronavirus vaccine comprising: (a) transfecting into a plurality of first cells: i) a nucleic acid encoding a coronavirus spike protein, and ii) a viral expression vector which comprises an indicator nucleic acid which produces a detectable signal; (b) incubating the first cells under conditions such that the first cells produce viral particles comprising the coronavirus spike protein; (c) contacting the viral particles of step (b) with a second cell in the presence of a sample obtained from the subject before the subject was exposed to a coronavirus vaccine or a sample from the subject obtained after the sample was exposed to the coronavirus vaccine, wherein the second cell expresses a cell surface receptor to which the coronavirus binds; (d) measuring the amount of the detectable signal produced by the second cell in order to determine the infectivity of the viral particles in the presence of the sample obtained before the subject was exposed to the coronavirus vaccine; and (e) measuring the amount of the detectable signal produced by the second cell in order to determine the infectivity of the viral particles in the presence of the sample obtained after the subject was exposed to the coronavirus vaccine; (f) comparing the amount of signal measured in step (d) with the amount of signal produced in step (e), and determining the level of a neutralizing antibody response in the sample based on the difference in the amount of signal measured in step (d) with the amount of signal produced in step (e).

In some embodiments of the methods disclosed herein, the antibody response may be a neutralizing antibody response that completely inhibits infection. In some embodiments of the methods disclosed herein, the neutralizing antibody response may partially inhibit infection, but to a level that is therapeutically effective.

In some embodiments of the methods disclosed herein, the coronavirus spike protein may be a coronavirus S protein. SARS CoV-2 Spike (S) protein is a trimeric protein that mediates the binding and entry of the virus into host cells. S protein is a major target of neutralizing antibodies. Each S protein monomer consists of an N-terminal S1 domain that mediates receptor binding and a membrane-proximal S2 domain that mediates membrane fusion. SARS CoV-2 can use the angiotensin converting enzyme-2 (ACE-2) as its cellular receptor.

The SARS CoV-2 S protein is known to mutate, leading to variants. SARS-CoV-2 variants are defied by specific point mutations along the length of the spike gene causing amino acid deletions or substitutions. These changers may confer enhanced spike protein binding efficiency to the ACE 2 receptor, allowing the virus to infect cells more readily. Additionally and/or alternatively, these changes may affect the capability of the virus to escape from antibodies that are raised after natural infection, after vaccine, or from antibody therapies. In some embodiments, the S protein may be from a subject infected with a severe acute respiratory syndrome coronavirus 2 (SARS-CoV-2) variant. In some embodiments the variant may be the B.1.1.7 (UK) variant, B.1.351 (South Africa) variant, the B.1.1.28.1 (Brazil) variant, or the B.1.427/B/1/429 (California) variant.

In some embodiments of the methods disclosed herein, the indicator nucleic acid may comprise an indicator gene. In some embodiments, the indicator gene may be a luciferase gene. Or other gene sequences that encode detectable indicators may be used.

Figure 2:
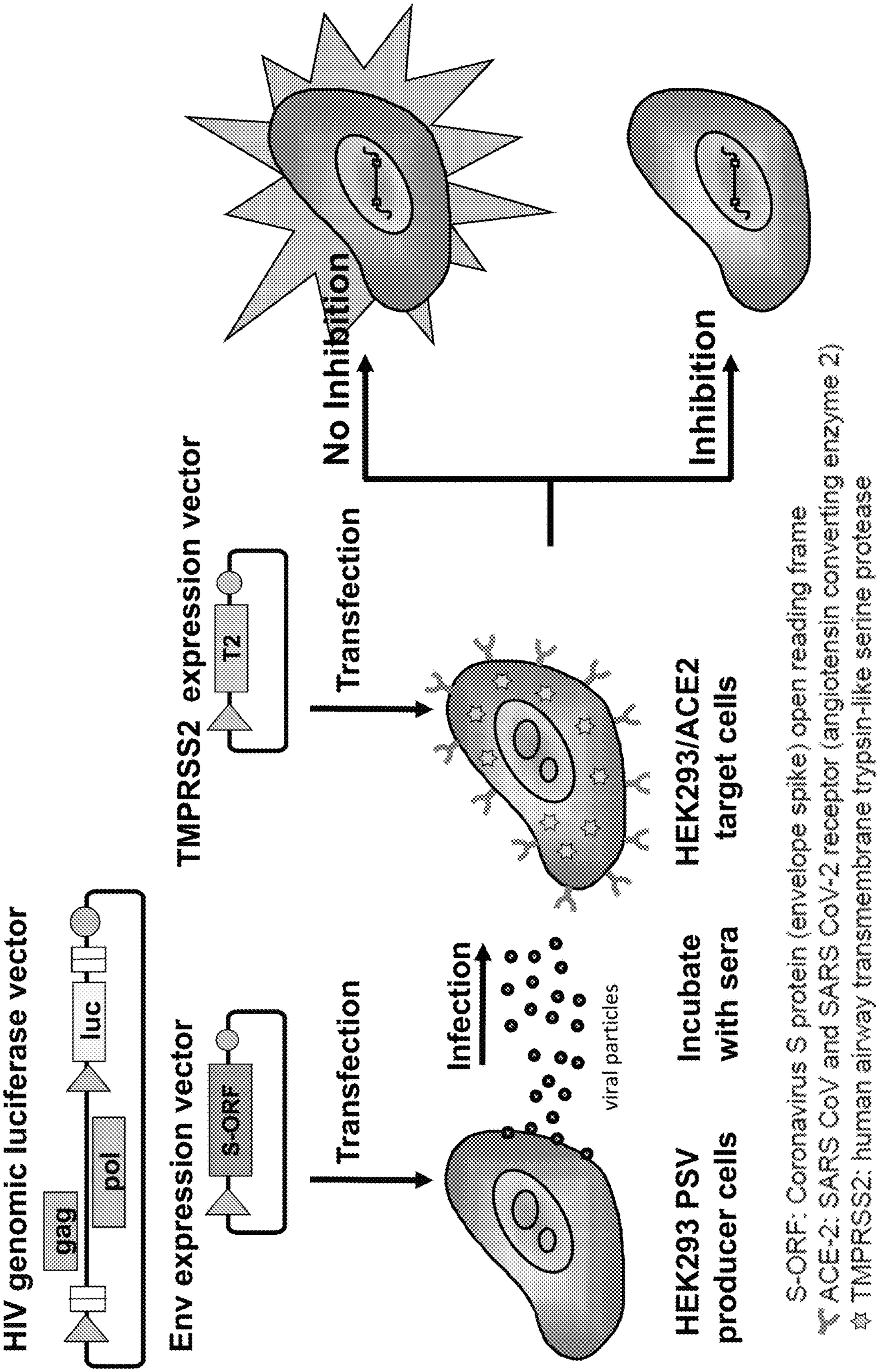
FIG. 2 depicts an example assay to detect coronavirus neutralizing antibodies in accordance with an embodiment of the disclosure wherein ACE-2 is stably expressed in target cells and TMPRSS2 is transiently expressed in target cells.
Figure 3:
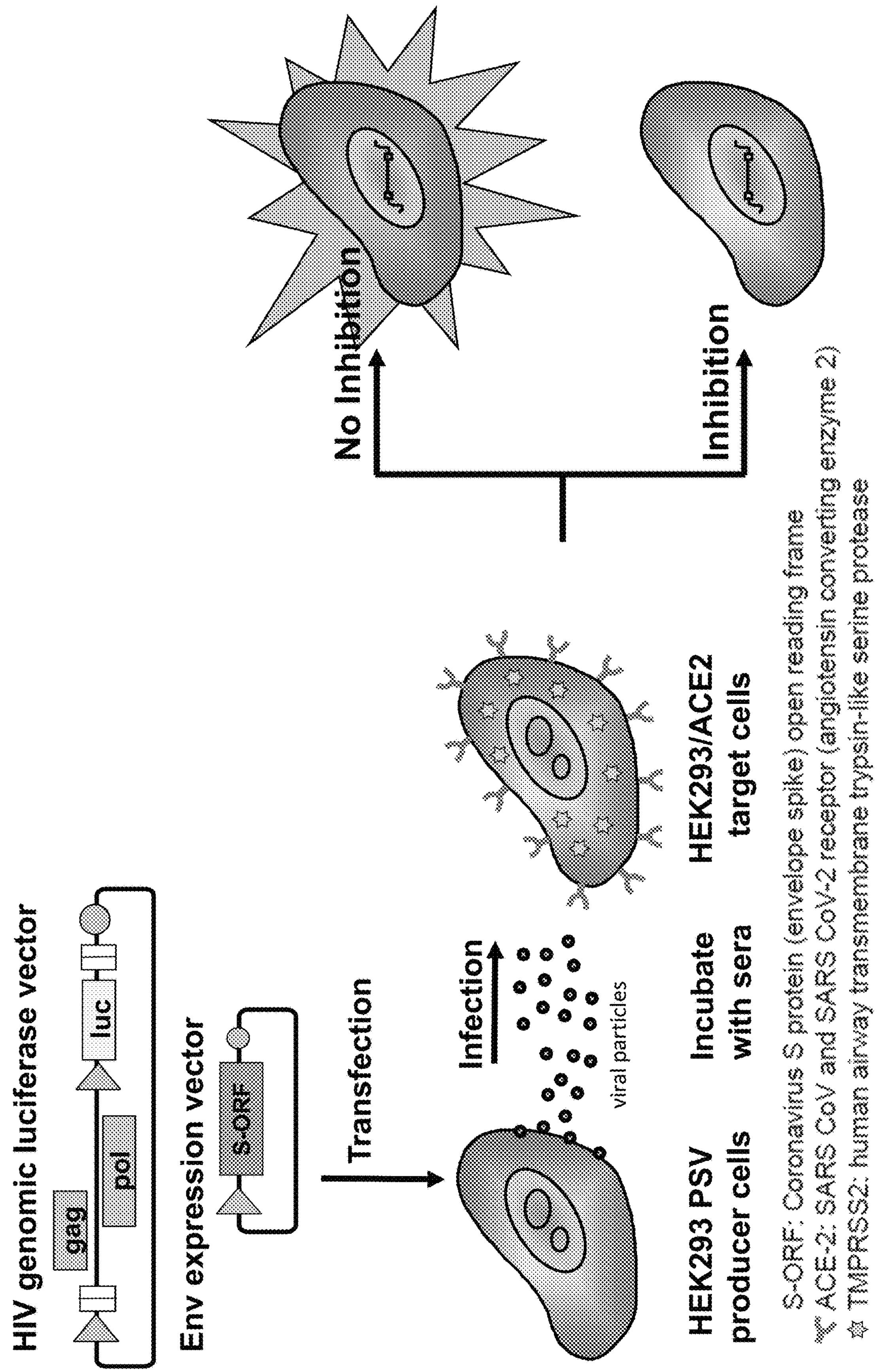
FIG. 3 depicts an example assay to detect coronavirus neutralizing antibodies in accordance with an embodiment of the disclosure wherein ACE-2 and TMPRSS2 are stably expressed in target cells.
Figure 4B:
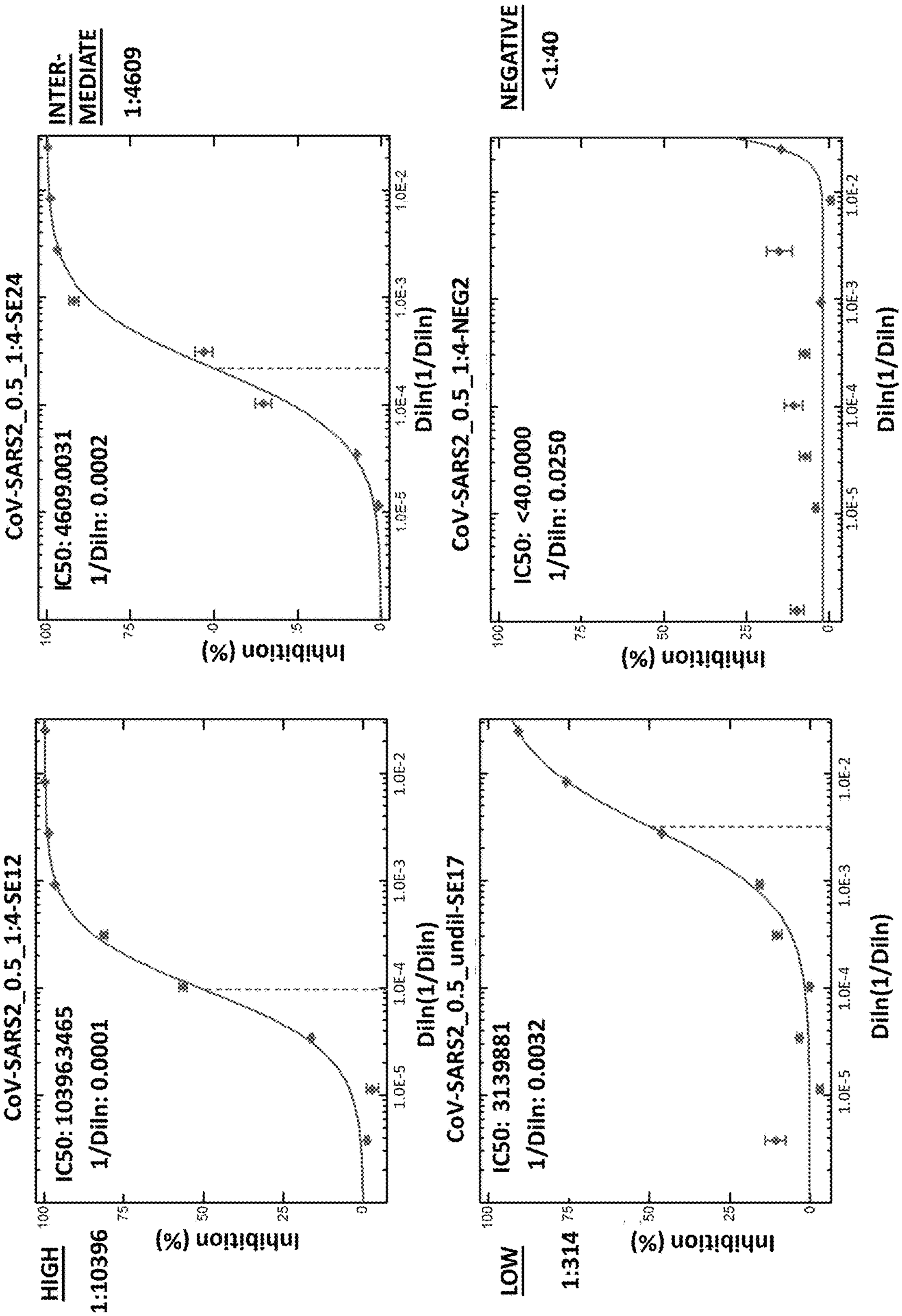
Figure 5B:
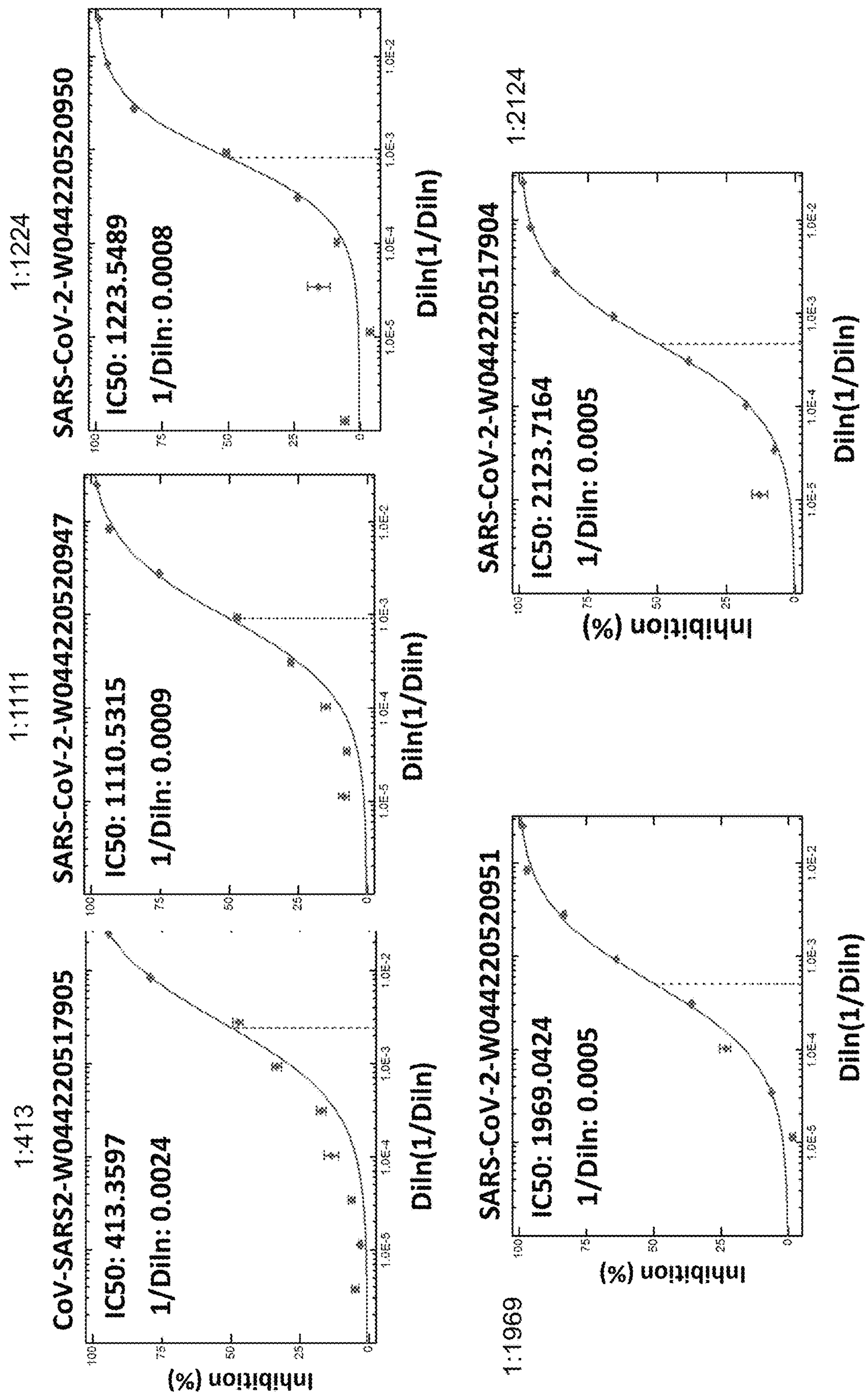

In some embodiments of the methods disclosed herein, the cell surface receptor may be ACE-2. As is depicted in FIG. 1, in some embodiments of the methods disclosed herein, the cell surface receptor, e.g., ACE-2, may be transiently expressed. As is depicted in FIG. 2 and FIG. 3, in some embodiments of the methods disclosed herein, the cell surface receptor, e.g., ACE-2, may be stably expressed. In some embodiments of the methods disclosed herein, the second cell may further express human airway transmembrane trypsin-like serine protease (TMPRSS2). As is depicted in FIG. 3, in some embodiments, both ACE-2 and TMPRSS2 may be stably expressed. In some embodiments, the cells may express a low level of ACE-2. In some embodiments, the cells may express an intermediate level of ACE-2. In some embodiments, the cells may express a high level of ACE-2.

In other aspects, disclosed are methods to evaluate mutations in SARS CoV-2 for their ability to confer increased or decreased susceptibility to anti-SARS CoV-2 neutralizing antibodies. For example, the method may comprise (a) transfecting into a first portion of a plurality of first cells: i) a nucleic acid encoding a control coronavirus spike protein, and ii) a viral expression vector which comprises an indicator nucleic acid which produces a detectable signal; and (b) transfecting into a second portion of a plurality of first cells: i) a nucleic acid encoding a coronavirus spike protein that comprises a mutation. The method may then further comprise (c) incubating the first and second portion of first cells separately under conditions such that the first portion cells produce first viral particles comprising the control coronavirus spike protein, and the second portion cells produce second viral particles comprising the coronavirus spike protein having the mutation. The method may further comprise (d) contacting the first viral particles of step (c) with a second cell in the presence of a sample comprising an antibody that recognizes SARS CoV-2 (i.e., an anti-SARS CoV-2 antibody), wherein the second cell expresses a cell surface receptor to which the coronavirus binds. The method may further comprise (e) contacting the second viral particles of step (c) with a second cell in the presence of a sample comprising an antibody that recognizes SARS CoV-2, wherein the second cell expresses a cell surface receptor to which the coronavirus binds. The method may further comprise (f) measuring the amount of the detectable signal produced by the second cells in (d) and (e), wherein a reduced amount of signal produced by the second cell in step (d) as compared to the signal produced by the second cell in step (e) indicates that the mutation in the spike protein confers a reduced susceptibility of the viral particles to the anti-SARS CoV-2 antibody. In certain embodiments, the control coronavirus spike protein is a spike protein from a wild type coronavirus. In certain other embodiments, the control coronavirus spike protein is a spike protein from a different subject or from the same subject at a different time point.

In other embodiments, the present disclosure provides a method for detecting the level of neutralizing antibody response (e.g., titer) to a mutated or variant SARS-CoV-2 in a subject previously exposed to a coronavirus vaccine developed for a non-mutated SARS-CoV-2 comprising: (a) transfecting into a plurality of first cells: i) a nucleic acid encoding a coronavirus spike protein (i.e., the mutated or variant spike protein), and ii) a viral expression vector which comprises an indicator nucleic acid which produces a detectable signal; (b) incubating the first cells under conditions such that the first cells produce viral particles comprising the mutant/variant coronavirus spike protein; (c) contacting the viral particles of step (b) with a second cell in the presence of a sample obtained from the subject before the subject was exposed to a coronavirus vaccine or a sample from the subject obtained after the sample was exposed to the coronavirus vaccine, wherein the second cell expresses a cell surface receptor to which the coronavirus binds; (d) measuring the amount of the detectable signal produced by the second cell in order to determine the infectivity of the viral particles in the presence of the sample obtained before the subject was exposed to the coronavirus vaccine; and (e) measuring the amount of the detectable signal produced by the second cell in order to determine the infectivity of the viral particles in the presence of the sample obtained after the subject was exposed to the coronavirus vaccine; (f) comparing the amount of signal measured in step (d) with the amount of signal produced in step (e), and determining the level of a neutralizing antibody response in the sample based on the difference in the amount of signal measured in step (d) with the amount of signal produced in step (e). In an embodiment, the spike protein of step (a) is isolated from the subject. In other embodiments, the spike protein is genetically modified in vitro. In some embodiments, the results with the mutated spike protein are compared to a normal (i.e., non-mutated) spike protein control.

In some embodiments, the coronavirus spike protein may comprise a mutation associated with increased viral infectivity. In come embodiments, the coronavirus spike protein may contain a D614G mutation. The mutation D614G in the carboxy terminal region of the SARS CoV-2 S1 domain is associated with increased viral loads in COVID-19 patients.

In some embodiments of the methods disclosed herein, the subject was infected with a coronavirus. In some embodiments of the methods disclosed herein, the subject was infected with severe acute respiratory syndrome coronavirus 2 (SARS CoV-2).

In some embodiments of the methods disclosed herein, the first cells may be mammalian cells. In some embodiments of the methods disclosed herein, the first cells may be human cells. In some embodiments of the methods disclosed herein, the first cells may be human embryonic kidney cells. In some embodiments of the methods disclosed herein, the human embryonic kidney cells may be 293 cells.

In some embodiments of the methods disclosed herein, the second cell may be a mammalian cell. In some embodiments of the methods disclosed herein, the second cell may be a human cell. In some embodiments of the methods disclosed herein, the second cell may be a human embryonic kidney cell. In some embodiments, the human embryonic kidney cell is a 293 cell. In certain embodiments, the second cell (also referred to herein as a target cell) is engineered to stably express ACE2 and/or TMPRSS2. In certain embodiments, the second cell is the 5A10 cell line, In certain embodiments, the second cell is the 5G7 cell line.

In some embodiments of the methods disclosed herein, the sample may be serum or plasma.

In some embodiments of the methods disclosed herein, the viral expression vector may be a human immunodeficiency virus (HIV) expression vector.

In some embodiments of the methods disclosed herein, the level of neutralizing antibody response of the sample is correlated to the subject's level of post-infection protective immunity.

In some embodiments of the methods disclosed herein, the level of neutralizing antibody response in the sample is correlated to a titer of total anti-coronavirus antibody as measured in the subject.

Compositions

Also disclosed are compositions for the detection of a compound such as a neutralizing antibody that can modulate SARS infectivity. In certain embodiments, the composition may comprise cells that have been engineered to be either producer cells or target cells as disclosed herein.

For example, the composition may comprise a cell (or cells) genetically modified to be a target cell that expresses an angiotensin-converting enzyme 2 receptor (ACE-2). In some embodiments, the target cell may be genetically modified to also express human airway transmembrane trypsin-like serine protease (TMPRSS2). In some embodiments, and as discussed herein, the ACE2 and/or TMPRSS2 may be introduced into the target cell in a manner that allows for transient expression. Or, the ACE2 and/or TMPRSS2 may be introduced into the target cell in a manner that allows for stable expression. In certain embodiments, the target cell is from the 5A10 cell line, In certain embodiments, the target cell is from the 5G7 cell line.

Additionally and/or alternatively, the composition may comprise a producer cell (or cells). In certain embodiments, the producer cell may comprise: i) a nucleic acid encoding a SARS CoV-2 spike protein or a portion thereof, and ii) a genomic viral expression vector comprising sequences from a second virus that is not a coronavirus and that comprises an indicator nucleic acid that produces a detectable signal. For example, in certain embodiments, the producer cell may be a genetically modified cell made by the steps of: transfecting into the cell: i) a nucleic acid encoding a SARS CoV-2 spike protein or a portion thereof, and ii) a genomic viral expression vector comprising sequences from a second virus that is not a coronavirus and that comprises an indicator nucleic acid that produces a detectable signal. In some embodiments, the coronavirus spike protein is a coronavirus S protein. In some embodiments, the viral expression vector comprising sequences from a second virus that is not a coronavirus and that comprises an indicator nucleic acid that produces a detectable signal is introduced into the cell in a manner that allows for transient expression. In some embodiments, the viral expression vector comprising sequences from a second virus that is not a coronavirus and that comprises an indicator nucleic acid that produces a detectable signal is introduced into the cell in a manner that allows for stable expression.

In certain embodiments, the second virus is HIV or a genetically modified HIV. Thus, in certain embodiments, disclosed is a composition comprising an HIV nucleic acid modified to remove genomic sequences that encode the HIV envelope protein and genetically modified to encode and express SARS CoV-2 spike protein or a portion thereof and/or cells transfected with an HIV nucleic acid modified encode and express SARS CoV-2 spike protein or a portion thereof.

A variety of constructs may be used as an indicator nucleic acid. In certain embodiments, the indicator nucleic acid comprises an indicator gene. For example, the indicator gene may be a luciferase gene. Or, other indicator genes may be used.

In certain embodiments, the S protein is from a subject infected with a coronavirus. In certain embodiments, the subject is infected with severe acute respiratory syndrome coronavirus 2 (SARS CoV-2). The SARS CoV-2 S protein is known to mutate, leading to variants. SARS-CoV-2 variants are defied by specific point mutations along the length of the spike gene causing amino acid deletions or substitutions. These changers may confer enhanced spike protein binding efficiency to the ACE 2 receptor, allowing the virus to infect cells more readily. Additionally, these changes may affect the capability of the virus to escape from antibodies that are raised after natural infection, after vaccine, or from antibody therapies. In some embodiments, the S protein may be from a subject infected with a severe acute respiratory syndrome coronavirus 2 (SARS-CoV-2) variant. In some embodiments the variant may be the B.1.1.7 (UK) variant, B.1.351 (South Africa) variant, the B.1.1.28.1 (Brazil) variant, or the B.1.427/B/1/429 (California) variant.

A variety of cells may be used to generate the target cell or the producer cell. In certain embodiments, the producer cells and/or the target cells are mammalian cells. Also, in some embodiments, the producer cells and/or the target cells are human cells. In some cases the producer cells and/or the target cells are human embryonic kidney (HEK) cells, as for example 293 HEK cells.

Kits

Also disclosed are kits for performing any of the steps of the disclosed methods and/or using any of the disclosed compositions and a computer-program product tangibly embodied in a non-transitory machine-readable storage medium (e.g., software) for performing any of the steps of the disclosed methods, and/or using any of the disclosed compositions, or running any of the parts of the disclosed systems.

Thus, the kit may comprise cells that have been engineered to be either producer cells or target cells as disclosed herein. In certain embodiments, the producer cell may comprise: i) a nucleic acid encoding a SARS CoV-2 spike protein or a portion thereof, and ii) a genomic viral expression vector comprising sequences from a second virus that is not a coronavirus and that comprises an indicator nucleic acid that produces a detectable signal. In certain embodiments, the producer cell may be made by the steps of: transfecting into a producer cell: i) a nucleic acid encoding a SARS CoV-2 spike protein or a portion thereof, and ii) a genomic viral expression vector comprising sequences from a second virus that is not a coronavirus and that comprises an indicator nucleic acid that produces a detectable signal.

Additionally and/or alternatively, the kit may comprise a target cell (or cells) that has been engineered to express an angiotensin-converting enzyme 2 receptor (ACE-2) and/or TMPRSS2. In some embodiments, and as discussed herein, the ACE2 and/or TMPRSS2 may be introduced into the target cell in a manner that allows for transient expression. Or, the ACE2 and/or TMPRSS2 may be introduced into the target cell in a manner that allows for stable expression. In an embodiment, the cells may comprise one of the 5A10 and/or 5G7 cell lines disclosed herein.

The kit may further comprise a reagent and/or equipment for contacting the target cell with a viral particle comprising at least a portion of the SARS CoV-2 spike protein in the absence and the presence of a compound to be tested as a potential modulator of SARS CoV-2 infectivity. In one embodiment, the compound may be a subject or a patient sample believed to contain neutralizing antibodies. Additionally, the kit may comprise a reagent and/or equipment and/or software for measuring levels of infection of the target cell in order to determine infectivity of the viral particle in the presence or absence of the compound. In one embodiment, infected cells may comprise a detectable marker. For example, in one embodiment, the target cells may comprise luciferase. Or, the viral particle may comprise the detectable marker (e.g., luciferase). Thus, in certain embodiments, the kit may comprise a reagent and/or equipment and/or software for measuring signal from the detectable marker (e.g., luciferase) due to infection of the target cells.

As disclosed herein, in certain embodiments, the viral particle is an HIV pseudovirion. For example, in one embodiment, the method may utilize the PhenoSense SARS CoV-2 neutralizing antibody (nAb) Assay format as disclosed herein.

The kit may further comprise reagents and/or equipment for incubating the producer cell under conditions such that pseudovirions that comprise the SARS CoV-2 spike protein or a portion thereof are generated. Also, the kit may comprise reagents and/or equipment for contacting the pseudovirions made by the producer cell with a target cell under conditions such that the pseudovirions infect the target cell and in the presence or absence of a compound to be tested as a potential modulator of SARS CoV-2 infectivity. In one embodiment, the compound may be a subject or patient sample believed to contain neutralizing antibodies.

Additionally, the kit may comprise a reagent and/or equipment and/or software for measuring levels of infection of the target cell in order to determine infectivity of the viral particle in the presence or absence of the compound. In one embodiment, infected cells may comprise a detectable marker. For example, in one embodiment, the target cells may comprise luciferase. Or, the viral particle may comprise luciferase. Thus, in certain embodiments, the kit may comprise a reagent and/or equipment and/or software for measuring signal from luciferase due to infection of the target cells.

Also disclosed is a computer-program product tangibly embodied in a non-transitory machine-readable storage medium, including instructions configured to use the kit and/or perform a step or steps of the kit of any of the disclosed embodiments. In one embodiment, the kit comprises a computer-program product tangibly embodied in a non-transitory machine-readable storage medium, including instructions configured to determine changes in SARS CoV-2 infectivity caused by a compound of interest.

Systems

Also disclosed are systems for performing any of the steps of the disclosed methods and/or using any of the disclosed compositions and computer-program product tangibly embodied in a non-transitory machine-readable storage medium (i.e., software) for performing any of the steps of the disclosed methods, and/or using any of the disclosed compositions, or running any of the parts of the disclosed systems.

Thus, the system may comprise cells that have been engineered to be either producer cells or target cells as disclosed herein. In certain embodiments, the producer cell may comprise: i) a nucleic acid encoding a SARS CoV-2 spike protein or a portion thereof, and ii) a genomic viral expression vector comprising sequences from a second virus that is not a coronavirus and that comprises an indicator nucleic acid that produces a detectable signal. In certain embodiments, the producer cell may be made by the steps of: transfecting into a producer cell: i) a nucleic acid encoding a SARS CoV-2 spike protein or a portion thereof, and ii) a genomic viral expression vector comprising sequences from a second virus that is not a coronavirus and that comprises an indicator nucleic acid that produces a detectable signal.

The target cell (or cells) may be engineered to express an angiotensin-converting enzyme 2 receptor (ACE-2) and/or TMPRSS2. In some embodiments, and as discussed herein, the ACE2 and/or TMPRSS2 may be introduced into the target cell in a manner that allows for transient expression. Or, the ACE2 and/or TMPRSS2 may be introduced into the target cell in a manner that allows for stable expression. In certain embodiments, the target cell is from the 5A10 cell line, In certain embodiments, the target cell is from the 5G7 cell line.

The system may further comprise a station and/or equipment for contacting the target cell with a viral particle comprising at least a portion of the SARS CoV-2 spike protein in the absence and the presence of a compound to be tested as a potential modulator of SARS CoV-2 infectivity. In one embodiment, the compound may be a subject or a patient sample believed to contain neutralizing antibodies. Additionally, the system may comprise a station and/or equipment for measuring levels of infection of the target cell in order to determine infectivity of the viral particle in the presence or absence of the compound. In one embodiment, infected cells may comprise a detectable marker. For example, in one embodiment, the target cells may comprise luciferase. Or, the viral particle may comprise the detectable marker (e.g., luciferase). Thus, in certain embodiments, the system may comprise a station for measuring signal from the detectable marker (e.g. luciferase) due to infection of the target cells.

As disclosed herein, in certain embodiments, the viral particle is an HIV pseudovirion. For example, in one embodiment, the method may utilize the PhenoSense SARS CoV-2 neutralizing antibody (nAb) Assay format as disclosed herein.

The system may further comprise a station and/or equipment for incubating the producer cell under conditions such that pseudovirions that comprise the SARS CoV-2 spike protein or a portion thereof are generated. Also, the system may comprise a station and/or equipment for contacting the pseudovirions made by the producer cell with a target cell under conditions such that the pseudovirions infect the target cell and in the presence or absence of a compound to be tested as a potential modulator of SARS CoV-2 infectivity. In one embodiment, the compound may be a subject or patient sample believed to contain neutralizing antibodies.

Additionally, the system may comprise a station and/or equipment for measuring levels of infection of the target cell in order to determine infectivity of the viral particle in the presence or absence of the compound. In one embodiment, infected cells may comprise a detectable marker. For example, in one embodiment, the target cells may comprise luciferase. Or, the viral particle may comprise luciferase. Thus, in certain embodiments, the system may comprise a station for measuring signal from luciferase due to infection of the target cells.

In some embodiments, the system or any of the stations of the system further comprises a computer and/or a data processor. In certain embodiments, the system may comprise one or more computers, and/or a computer product tangibly embodied in a non-transitory computer readable storage medium containing instructions which, when executed on the one or more data processors, cause the one or more data processors to perform actions for performing the methods or implementing the systems of any of embodiments disclosed herein. One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines. For example, as disclosed below, the system may comprise a computer and/or computer-program product tangibly embodied in a non-transitory machine-readable storage medium for relating changes in infectivity of the viral particles or pseudovirions to an autoimmune response. Thus, in certain embodiments, the system may comprise components to quantify the measurement. Also, the system may comprise components to perform statistical analysis of the data.

Also disclosed is a computer-program product tangibly embodied in a non-transitory machine-readable storage medium, including instructions configured to run the systems and/or perform a step or steps of the methods of any of the disclosed embodiments. In one embodiment, the system comprises a computer-program product tangibly embodied in a non-transitory machine-readable storage medium, including instructions configured to determine changes in SARS CoV-2 infectivity caused by a compound of interest.

EXAMPLES

Example 1—SARS CoV-2 Neutralizing Antibody Assay

The SARS CoV-2 nAb Assay has been developed by leveraging the proprietary PhenoSense Assay platform that was developed to evaluate antiretroviral drug susceptibility (Petropoulos et al., Antimicrob. Agents Chemother. 44:920-28, 2000) and later adapted to evaluate entry inhibitors, nAb activity (Richman et al., PNAS 100:4144-49, 2003) and co-receptor tropism (Whitcomb et al., Antimicrob. Agents Chemother. 51:566-75, 2007). The production of luciferase is dependent on virus entry and the completion of a single round of virus replication. Agents that inhibit pseudovirus entry or replication reduce luciferase activity in a dose-dependent manner, providing a quantitative measure of drug and antibody susceptibility. Over time, the PhenoSense assay platform has been successfully adapted to evaluate vaccines and entry inhibitors that target a variety of enveloped viruses, including Orthomyxovirus (Influenza A & B), Paramyxovirus (RSV A & B), Filovirus (Ebola), and most recently Coronavirus (SARS CoV-2, SARS CoV).

The measurement of nAb activity using the PhenoSense SARS CoV-2 nAb Assay is performed by generating HIV-1 pseudovirions that express the SARS CoV-2 spike protein (See, e.g., FIGS. 1-3). The pseudovirus is prepared by co-transfecting HEK293 producer cells with an HIV-1 genomic vector and a SARS CoV-2 envelope expression vector. Neutralizing antibody activity is measured by assessing the inhibition of luciferase activity in HEK293 target cells expressing the ACE2 receptor following pre-incubation of the pseudovirions with serial dilutions of the serum specimen. The expression of luciferase activity in target cells is inhibited in the presence of anti-SARS CoV-2 nAb. Data are displayed by plotting the percent inhibition of luciferase activity vs. $\log_{10}$ reciprocal of the serum/plasma dilution and nAb titers are reported as the reciprocal of the serum dilution conferring 50% inhibition ($ID_{50}$) of pseudovirus infection (Equation 1 below).

% Inhibition=100%−(((RLU(Vector+Sample+Diluent)−RLU(Background))/(RLU(Vector+Diluent)−RLU(Background)))×100%)  Equation 1:

The results of the PhenoSense SARS CoV-2 nAb can be reported as an $ID_{50}$ titer (1/Dilution) or qualitatively (positive, negative) based on a pre-defined dilution cutoff (e.g >50% inhibition at 1:40 dilution). Examples of Anti-SARS CoV-2 nAb titration profiles can be found in FIGS. 4A, 4B, 5A and 5B.

To ensure that the measured nAb activity is SARS CoV-2 nAb specific, each test specimen is also assessed using a non-specific pseudovirus (specificity control) that expresses a non-reactive envelope protein of one or more unrelated viruses (e.g. avian influenza virus).

Critical Reagents

A critical reagent is defined as an assay component essential to obtaining the anti-SARS CoV-2 nAb titer. Critical reagents for the anti-SARS CoV-2 nAb assay include the following:

1. PhenoSense SARS CoV-2 Pseudovirus (Monogram Biosciences)
2. PhenoSense SARS CoV-2 "Specificity Control" Pseudovirus (Monogram Biosciences)
3. Pseudovirus Producer Cells: HEK293VL (Monogram Biosciences)
4. Pseudovirus Target Cells: HEK293ACE2 (Monogram Biosciences)
   a) Transient ACE2 expression
   b) Stable ACE2 expression (e.g., cell lines 5A10 and 5G7)
5. Assay Controls (Monogram Biosciences)
   a) Positive Control Serum: pooled SARS CoV-2 antibody positive human sera
      i. The anti-SARS CoV-2 titer of the Positive Control Serum must be qualified at ≥360.
      ii. The anti-Specificity Control titer of the Positive Control Serum must be qualified at ≤40.
   b) Negative Control Serum: pooled SARS CoV-2 antibody negative human sera, or human sera collected prior to the SARS CoV-2 pandemic (pre-2019)
      i. The anti-SARS CoV-2 titer of the Negative Control Serum must be qualified at ≤40.
      ii. The anti-Specificity Control titer of the Negative Control Serum must be qualified at ≤40.

Instrumentation

1. BioCube Luciferase Reading System: A custom built, fully-automated and integrated bar-code driven system designed and validated to dispense cell lysis/luciferase reaction components and measure luciferase activity (relative light units (RLU)) using a luminometer.
2. Data Analysis Pipeline: A custom built, integrated system that is designed and validated to (a) accept output files from the Luciferase Reading System, (b) apply luciferase activity based on the assay plate map to generate nAb inhibition curves, (c) assess assay performance (RLU, CV), (d) generate quantitative measures of nAb activity (e.g. $ID_{50}$ titer), and (e) assign a qualitative assessment of nAb activity (Positive, Negative) based on a comparison of the anti-SARS CoV-2 to the corresponding anti-Specificity Control titer.

Acceptance Criteria

1. Assay Specimen Plate Acceptance (SARS CoV-2 Pseudovirus Plate)

Assay specimen plates will be deemed acceptable when the following parameters are met:

a) The anti-SARS CoV-2 titer of the Positive Control Serum varies ≤3-fold (one serial dilution) from the qualified Positive Control Serum titer.
   i. The qualified anti-SARS Cov-2 titer of the Positive Control Serum must be ≥400.
b) The anti-SARS CoV-2 titer of the Negative Control Serum varies ≤3-fold (one serial dilution) from the qualified Negative Control Serum titer.
   i. The qualified anti-SARS CoV-2 titer of the Negative Control Serum must be ≤40.

2. Assay Specificity Plate Acceptance (Specificity Control Pseudovirus Plate)

Assay specificity plates will be deemed acceptable when the following parameters are met:

a) The anti-Specificity Control titer of the Positive Control Serum is ≤3-fold (one serial dilution) from the qualified Positive Serum Control titer.
   i. The qualified anti-Specificity Control titer of the Positive Control Serum must be ≤400.
b) The anti-Specificity Control titer of the Negative Control Serum varies ≤3-fold (one serial dilution) from the qualified Negative Serum Control titer.
   i. The qualified anti-Specificity Control titer of the Negative Control Serum must be ≤40.

3. Assay Specimen Titer Determination

Assay specimens will be reported as "Positive" and a numeric titer is reported when:

a) The anti-SARS CoV-2 nAb titer ($ID_{50}$) is ≥3-fold higher than the corresponding anti-Specificity Control titer.

Assay specimens will be reported as "Negative" and a numeric titer is not reported when:

a) The anti-SARS CoV-2 nAb titer ($ID_{50}$) is <3-fold higher than the corresponding anti-Specificity Control titer.

Example 2—Assay Accuracy and Inclusivity

Assay Accuracy and Inclusivity was determined by assessing the nAb titers exhibited in serology confirmed SARS CoV-2 Positive/Reactive and Negative/Non-Reactive sera, or samples collected prior to 2019.

a) SARS CoV-2 Positive Samples—Approximately 45 human sera/plasma specimens confirmed positive for SARS CoV-2 antibody based on IgG and/or IgM reactivity.
b) SARS CoV-2 Negative Samples—Approximately 45 human sera/plasma specimens confirmed negative for SARS CoV-2 antibody base on IgG and/or IgM reactivity
c) Historic Negative Samples—Approximately 30 human sera/plasma specimens collected prior to the SARS CoV-2 pandemic (pre-2019).

Figure 9:
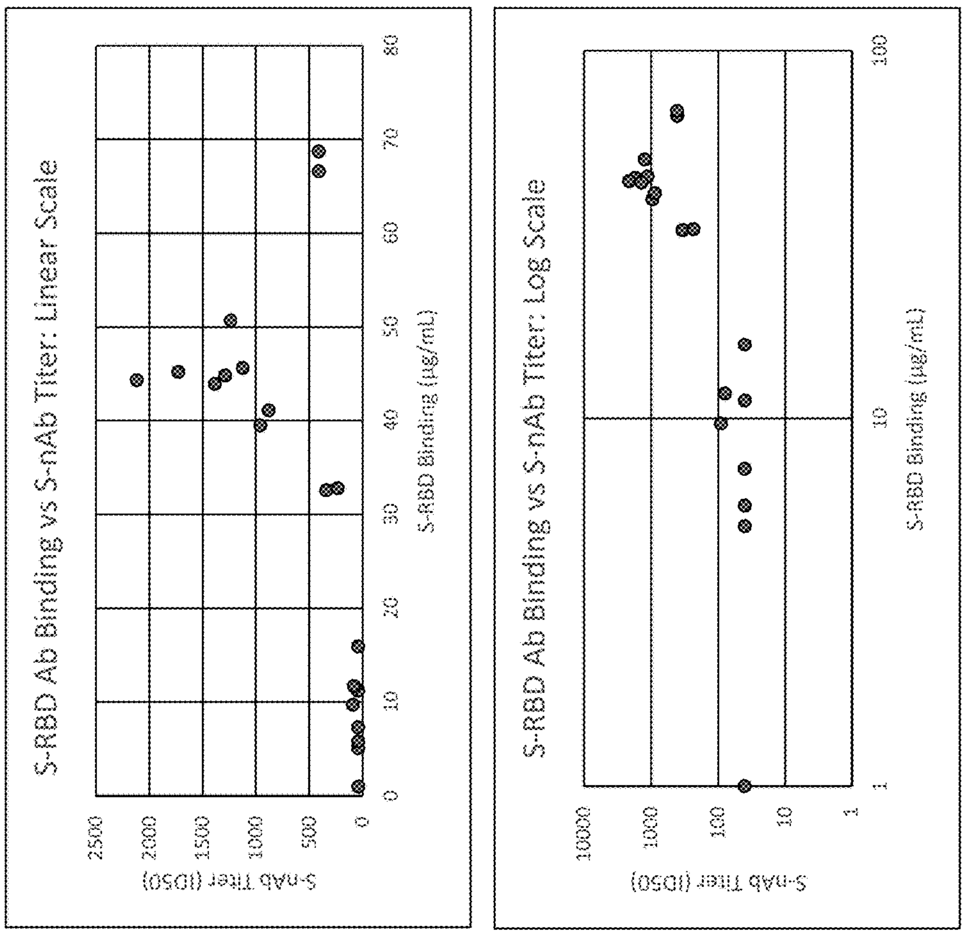
FIG. 9 depicts a correlation of results of anti-SARS CoV-2 receptor binding domain assays and anti-SARS CoV-2 nAb titers generated using an embodiment of the assay disclosed herein and plotted as a linear (upper) or log scale (lower) comparison.

Serology Positive specimens are defined as IgG or total Ig positive as determined using antibody binding assays. Serology Negative samples are defined as IgG or Total Ig negative as determined using antibody binding assays. Historical Negative samples are defined as samples with collection dates that pre-date the SARS CoV-2 pandemic. All serology positive SARS CoV-2 Positive/Reactive sera were confirmed SARS CoV-2 PCR Positive and all SARS CoV-2 Negative/Non-Reactive sera were confirmed SARS CoV-2 PCR Negative. Examples of correlations between the results of the antibody binding assays and nAb titers generated using the assay disclosed herein are in FIGS. 8 and 9.

Assay Accuracy and Inclusivity test results are recorded in FIG. 10.

Based on the combined results of qualitative serology and PCR assays, the sensitivity of the PhenoSense anti-SARS CoV-2 Assay is 100% (no false negatives among 49 samples), and the specificity is 98% (one false positive among 50 samples). The single false positive result occurred at the 1:40 minimum required dilution.

Based on the combined results of qualitative serology assays and historic negative samples, the specificity of the PhenoSense anti-SARS CoV-2 nAb assay is 98.8% (one false positive among 82 samples).

The acceptance criteria for quantitative determinations of nAb titer were not pre-defined. The qualitative assessment of SARS CoV-2 nAb positive and negative samples satisfied the pre-defined acceptance criteria:

a) ≥75% of serology positive samples must generate a Positive, nAb detected result.
b) ≥75% of serology negative samples must generate a Negative, nAb not detected result.
c) ≥90% of historic negative samples must generate a Negative, nAb not detected result.

Example 3—Intra-Assay Precision

Intra-Assay Precision was determined by assessing the variation in $ID_{50}$ observed across six replicates of four serum samples consisting of a nAb High-Titer Positive, Intermediate-Titer Positive, Low-Titer Positive and Negative sample.

a) High Titer Sera—Human sera exhibiting high titer anti-SARS CoV-2 nAb activity: $ID_{50}$>1:5000
b) Intermediate Titer Sera—Human sera exhibiting intermediate titer anti-SARS CoV-2 nAb activity: 1:5000≥$ID_{50}$≥1:1000
c) Low Titer Sera—Human sera exhibiting low titer anti-SARS CoV-2 nAb activity: $ID_{50}$<1:1000
d) Negative Human Sera—Human sera lacking anti-SARS CoV-2 nAb activity: $ID_{50}$<1:40

Intra-Assay Precision was evaluated within each of four separate assay runs.

a) One assay run (six replicates of four serum samples) was conducted by preparing serum dilutions using a manual method and inoculation of HEK293 cells transiently expressing ACE2.
b) One assay run (six replicates of four serum samples) was conducted by preparing serum dilutions using a manual method and inoculation of HEK293 cells stably expressing ACE2.
c) One assay run (six replicates of four serum samples) was conducted by preparing serum dilutions using an automated method and inoculation of HEK293 cells transiently expressing ACE2.
d) One assay run (six replicates of four serum samples) was conducted by preparing serum dilutions using an automated method and inoculated HEK293 cells stably expressing ACE2.

Intra-Assay Precision test results are recorded in FIG. 11, FIG. 12, FIG. 13, and FIG. 14.

The assessment for each arm of Intra-Assay Precision satisfied the pre-defined acceptance criteria:

a) The High Titer Sample must exhibit $ID_{50}$ variation ≤3-fold (one serial dilution)
b) The Intermediate Titer Sample must exhibit $ID_{50}$ variation ≤3-fold.
c) The Low Titer Sample must exhibit $ID_{50}$ variation ≤3-fold.
d) The Negative Sample must exhibit $ID_{50}$ variation ≤3-fold.

Example 4—Inter Assay Precision

Inter-Assay Precision was determined by assessing the variation in $ID_{50}$ mean observed across six replicates of four serum samples consisting of a High-Titer Positive, Intermediate-Titer Positive, Low-Titer Positive and Negative sample (Precision and Reproducibility Panel).

a) High Titer Sera—Human sera exhibiting high titer anti-SARS CoV-2 nAb activity: $ID_{50}$>1:5000
b) Intermediate Titer Sera—Human sera exhibiting intermediate titer anti-SARS CoV-2 nAb activity: 1:5000≥$ID_{50}$≥1:1000
c) Low Titer Sera—Human sera exhibiting low titer anti-SARS CoV-2 nAb activity: $ID_{50}$<1:1000
d) Negative Human Sera—Human sera lacking anti-SARS CoV-2 nAb activity: $ID_{50}$<1:40

Inter-Assay Precision was evaluated across all four independent runs performed by two operators using two independent lots of critical reagents (pseudovirus, cells, assay controls).

A) One assay run (six replicates of four serum samples) was conducted by preparing serum dilutions using a manual method and inoculation of HEK293 cells transiently expressing ACE2.
B) One assay run (six replicates of four serum samples) was conducted by preparing serum dilutions using a manual method and inoculation of HEK293 cells stably expressing ACE2.

C) One assay run (six replicates of four serum samples) was conducted by preparing serum dilutions using an automated method and inoculation of HEK293 cells transiently expressing ACE2.

D) One assay run (six replicates of four serum samples) was conducted by preparing serum dilutions using an automated method and inoculated HEK293 cells stably expressing ACE2.

Figure 7:
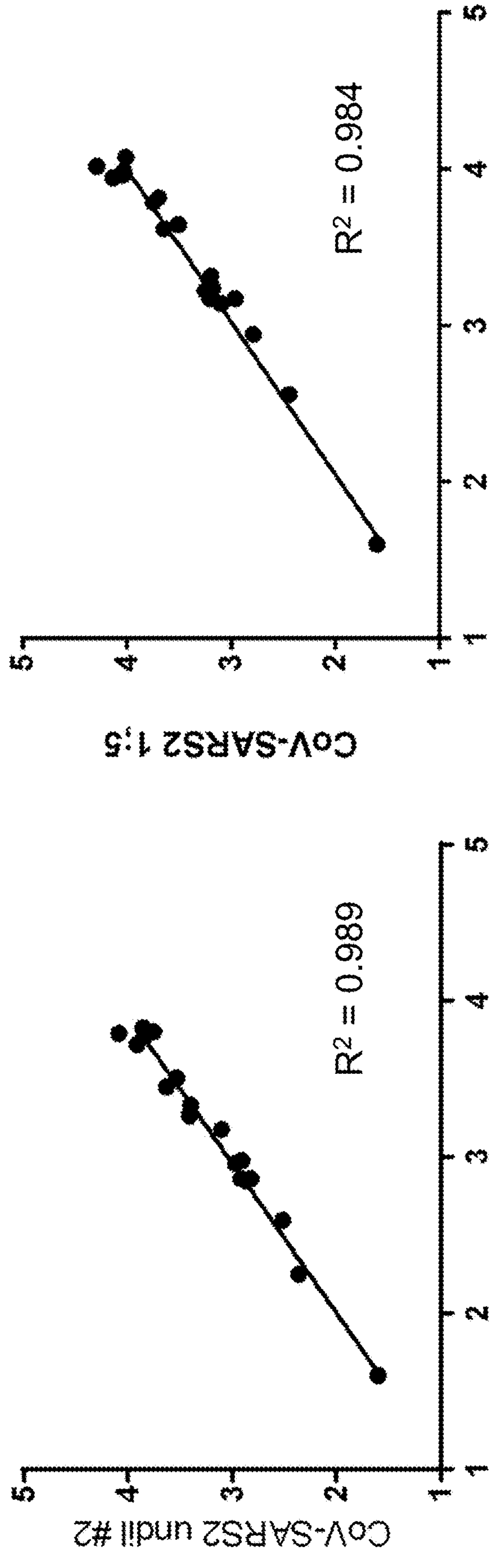
FIG. 7 depicts a chart analyzing the reproducibility of an anti-SARS CoV-2 nAb assay carried out according to an embodiment of the disclosure.

Inter-Assay Precision test results are recorded in FIG. 15. A graphic analysis of the reproducibility of an anti-SARS CoV-2 nAb assay carried out according to an embodiment of the disclosure is depicted in FIG. 7.

The assessment across all arms of Inter-Assay Precision satisfied the pre-defined acceptance criteria:

a) The High Titer Sample must exhibit $ID_{50}$ variation ≤3-fold (one serial dilution)

b) The Intermediate Titer Sample must exhibit $ID_{50}$ variation ≤3-fold.

c) The Low Titer Sample must exhibit $ID_{50}$ variation ≤3-fold.

d) The Negative Sample must exhibit $ID_{50}$ variation ≤3-fold.

The contribution of manual versus automated serum dilution and transient versus stable ACE2 expression to Inter-Assay Precision were interrogated using appropriate statistical methods.

Manual vs. Automated Serum Dilution

The inter-assay precision of assays conducted using manual and automated serum dilutions were also compared to assess the equivalence of the two dilution methods. Comparative results of the manual and automated dilution processes are recorded in FIG. 16. Observed differences in $ID_{50}$ mean and $ID_{50}$ median were <1.5-fold.

Transient vs. Stable ACE2 Expression

The inter-assay precision of assays conducted using HEK293 cells that transiently or stably express ACE2 was compared to assess the equivalence of the two target cell types. Comparative results of the ACE2 transient and stable cell types are recorded in FIG. 17. Observed differences in $ID_{50}$ mean and $ID_{50}$ median were <2-fold.

Inter-Assay Run Comparison

Across all possible paired comparisons, differences in mean $ID_{50}$ for the HTS, ITS and LTS samples did not exceed 3-fold, satisfying the pre-defined acceptance criteria An ANOVA analysis comparing Runs A, B, C, D indicated differences in Runs A, B, C, D. Based on a Tukey Honest Significant Differences test, the difference was entirely driven by the results of Run A compared to Runs B, C, D. Additional studies are planned to investigate the potential sources of the observed variation. Currently, the preferred assay modality corresponds to Run C (automated sample dilution, transient ACE2 expression), which does not differ significantly modalities of Run B (manual sample dilution, stable ACE2 expression) and Run D (automated sample dilution, stable ACE2 expression).

Example 5—Assay Linearity

Figure 19:
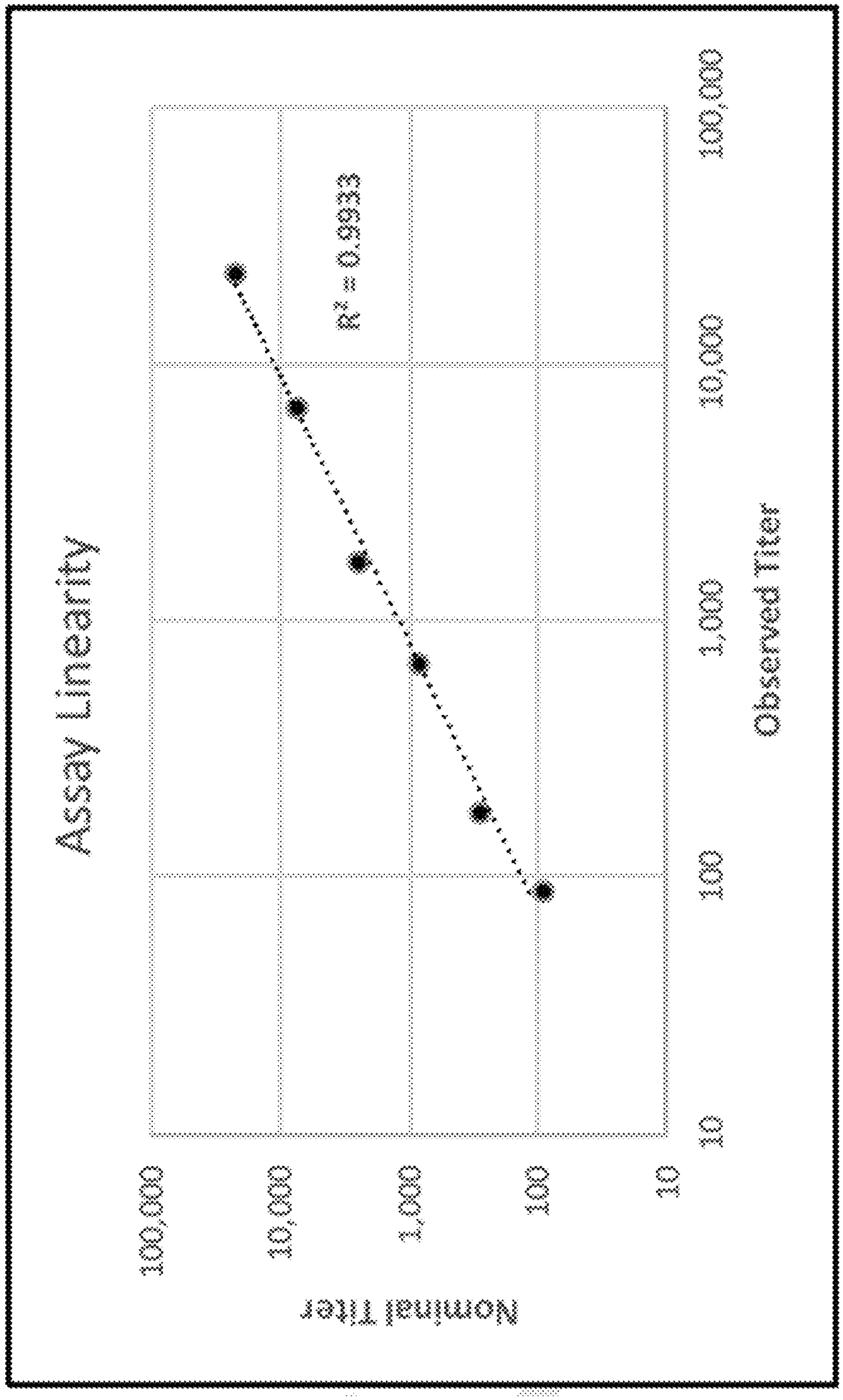
FIG. 19 depicts a chart showing an interrogation of assay linearity using linear regression testing in accordance with an embodiment of the disclosure.

Assay Linearity was determined by creating and testing five three-fold dilutions (approximately one half log 10) of a High-Titer Positive serum in negative serum. Each dilution was tested independently in the assay. A serum with an $ID_{50}$ titer of 22,224 was used to generate six contrived samples with nominal (expected) $ID_{50}$ titers of 7408, 2469, 823, 274, 123, 91. The observed titers of each of the contrived samples was compared to the nominal titers based on the undiluted sample $ID_{50}$ (FIG. 18). Assay linearity was interrogated using standard statistical methods, e.g. linear regression testing (FIG. 19).

Assay linearity satisfied the pre-defined acceptance criteria: The variation in true (observed) titer ($ID_{50}$) extrapolated from each neighboring start dilution of the linearity sample must exhibit ≤3-fold variation (observed titer÷predicted titer ≤3-fold).

Example 6—Assay Specificity

Specificity was evaluated by assessing assay reactivity (true positives), assay cross-reactivity (false positives) and assay interference (false negatives). Specificity testing was performed using a High-Titer Positive, Intermediate-Titer Positive, Low-Titer Positive and Negative sample (Assay Specificity Panel).

a) High Titer Sera—Human sera exhibiting high titer anti-SARS CoV-2 nAb activity: $ID_{50}$>1:5000 b) Intermediate Titer Sera—Human sera exhibiting intermediate titer anti-SARS CoV-2 nAb activity: 1:5000≥$ID_{50}$≥1:1000 c) Low Titer Sera—Human sera exhibiting low titer anti-SARS CoV-2 nAb activity: $ID_{50}$<1:1000 d) Negative Human Sera—Human sera lacking anti-SARS CoV-2 nAb activity: $ID_{50}$<1:40

Reactivity

Assay reactivity was evaluated by depleting the immunoglobulin of two low-titer anti-SARS CoV-2 nAb samples (LTS-1, LTS-2) and one negative titer sample (NTS) and assessing the impact on anti-SARS CoV-2 nAb activity. Antibody depletion was performed using protein G sepharose affinity chromatography.

The depletion on anti-SARS CoV-2 nAb activity is recorded in FIGS. 20 and 21. It is expected that multiple rounds of protein G affinity chromatography would be required to completely deplete immunoglobulin and the associated anti-SARS CoV-2 nAb activity.

The results of assay reactivity testing satisfied the pre-defined assay acceptance criteria:

a) Depletion of immunoglobulin must reduce the nAb titer of the Low Titer Serum Samples (fold reduction >1).

b) The inhibition of a majority of serum serial dilutions exhibiting >30% inhibition prior to immunoglobulin depletion must exhibit a reduction in % inhibition following immunoglobulin depletion.

Cross-Reactivity/Selectivity

Assay cross reactivity/selectivity was evaluated based on two approaches:

a) SARS CoV-2 and SARS CoV pseudoviruses were assessed for non-specific nAb by evaluating 32 archived serum samples with a collection date (2017) that precede the SARS CoV-2 pandemic. i.e., Historic Negative (HN) samples.

The summary results of non-specific nAb activity in pre-pandemic HN sera are recorded in FIG. 22. Anti-SARS CoV-2 nAb activity was not detected in HN samples (0/32). Low levels of anti-SARS CoV activity was observed in 15/32 (47%) samples.

b) SARS CoV-2 and SARS CoV pseudoviruses were assessed for non-specific nAb activity using negative serum samples spiked with high concentrations of antibodies directed to three viruses (HIV, HBV, HCV) that are likely to be represented in this pre-pandemic specimen panel; along with SARS CoV.

nAb activity observed in the presence of high concentrations (200 μg/mL) of antiviral antibodies was compared to nAb activity in the presence of antiviral antibody vehicle alone (FIG. 23). Non-specific anti-SARS CoV-2 nAb activity was not detected in four HN samples spiked with anti-viral antibodies. Two of the four HN samples exhibited low level nAb activity against SARS CoV in the presence and absence (vehicle only) of anti-viral nAb.

The results of cross reactivity testing satisfied the pre-defined assay acceptance criteria.

a) ≥90% of historic negative samples (e.g. 27/30) must generate a Negative, nAb not detected result.

b) Addition of antiviral antibodies must not increase the SARS CoV-2 nAb titer of negative sera by ≥3-fold (one serial dilution) above the nAb titer observed with vehicle alone, with the notable exception of the anti-SARS CoV antibody.

Interference

Interference by endogenous and exogenous agents was evaluated.

a) Endogenous interference testing was performed to determine whether anti-SARS CoV-2 nAb activity can be reliably detected in certain matrices and whether the matrix impacted detection. Aberrant matrices including hemolytic (hemoglobin), lipemic (triglyceride), icteric (bilirubin) and proteinemic (albumin) serum samples were evaluated. Final concentrations were as designated in CLSI EP07-A2.

The results of sample matrix interference testing are recorded in FIG. 24. No evidence of interference was observed using serum specimens exhibiting high, intermediate, low and negative anti-SARS CoV-2 nAb activity.

b) Exogenous interference testing was performed to determine whether anti-SARS CoV-2 nAb activity can be reliably detected in the presence of exogenous components, specifically components in blood collection devices/tubes. Sera and plasma from multiple (29) donors were tested and compared.

Figure 6:
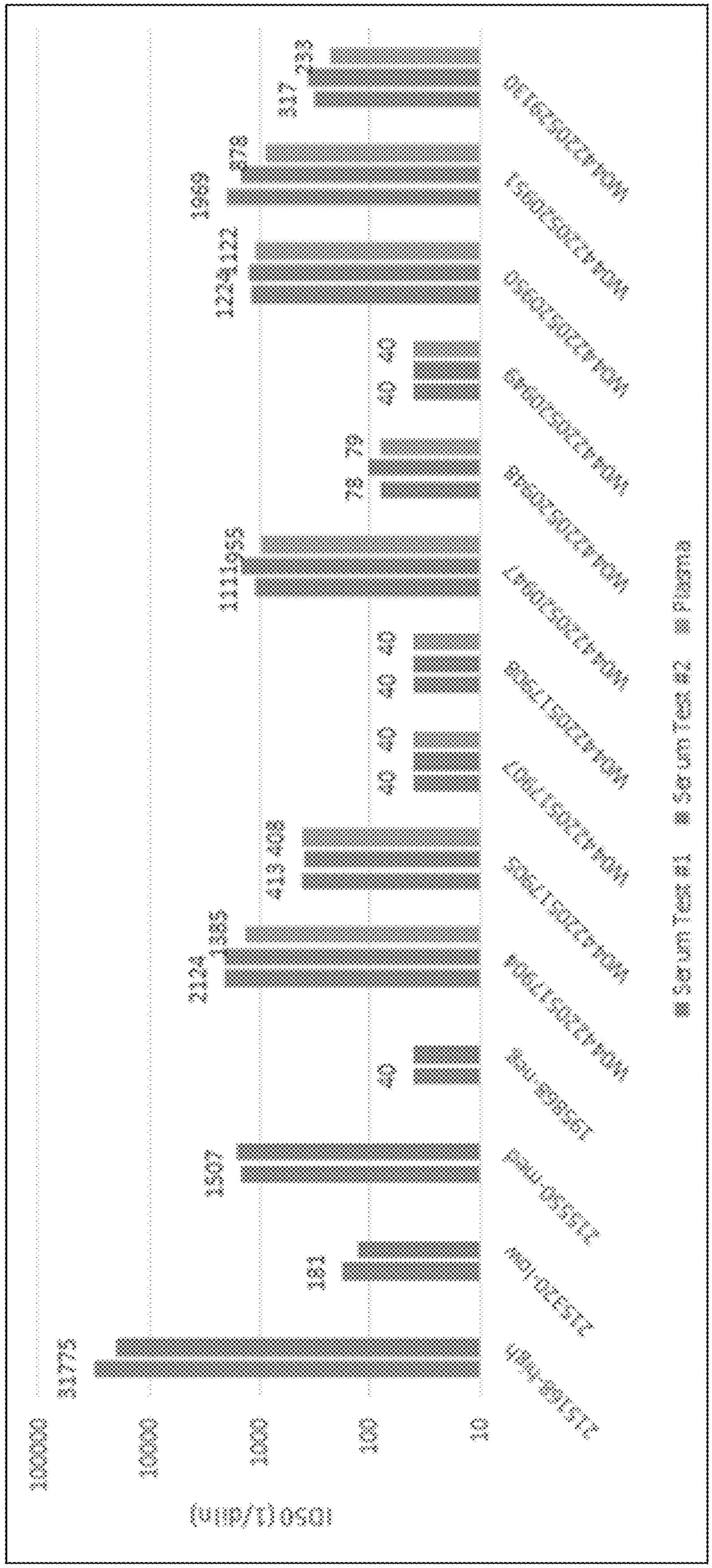
FIG. 6 depicts a chart comparing anti-SARS CoV-2 nAb titers from assays conducted in duplicate with convalescent sera and, in some cases, with anti-SARS CoV-2 nAb titers in plasma from the same subjects in accordance with an embodiment of the disclosure. The titers were generated in accordance with an embodiment of the disclosure. In each of the groupings, the first (left-most) bar is serum test 1, the second bar is serum test 2, and when present the third (right-most) bar is plasma. Sample identifiers are shown on the x-axis and the titer (ID50=1/dilution for 50% inhibition) is shown on the y-axis.

Interference related to specimen type/collection is recorded in FIG. 25. Significant differences in assay results based on specimen type were not observed. Comparisons of anti-SARS CoV-2 nAb titers in convalescent sera and plasma can be seen in FIG. 6. Four discordant qualitative assessment of anti-SARS CoV-2 nAb activity for serum and plasma pairs occurred at low titer or in the presence of non-specific inhibition based on the assay specificity control result. The quantitative assessments of nAb titer for these four sample pairs were comparable.

The results of interference testing satisfied the pre-defined assay acceptance criteria:

a) Addition of hemoglobin, bilirubin, triglyceride or albumin must not increase or decrease the SARS CoV-2 nAb titer of High Titer, Intermediate Titer, Low Titer or Negative samples by ≥3-fold (one serial dilution) above or below the nAb titer observed with vehicle alone.

b) Serum and plasma sample collections will be considered equivalent if SARS CoV-2 titers do not differ by ≥3-fold (one serial dilution).

Example 7—Assay Sensitivity

The ability of the assay to reliably assess anti-SARS CoV-2 nAb activity at the 1:40 assay MRD was interrogated using two anti-SARS CoV-2 Low Titer Positive Sera that were diluted 1:2 and 1:3 and tested in the assay in triplicate in two separate assay runs. Thus, Anti-SARS CoV-2 nAb Positive Serum diluted in Negative Serum to achieve nominal titers of 1:60 and 1:40.

The results of Sensitivity testing are recorded in FIG. 26. Low Titer Positive Sera consistently resulted positive (6/6 replicates) and the 1:3 dilution of Low Titer Positive Sera consistently resulted negative (6/6 replicates).

The results of sensitivity testing satisfied the pre-defined assay acceptance criteria:

a) A majority (e.g. 4/6) of anti-SARS CoV-2 nominal low titer (~1:60) positive serum replicates must result Positive, nAb detected for anti-SARS CoV-2 nAb activity.

b) A majority (e.g. 4/6) of anti-SARS CoV-2 nominal low titer (~1:20) negative serum replicates must result Negative, nAb not detected.

c) A majority (e.g. 4/6) of anti-SARS CoV-2 negative serum replicates must result Negative, nAb not detected.

Example 8—Assay Stability

Sample and reagent stability was demonstrated by evaluating the consistency of anti-SARS CoV-2 nAb activity over time and under different storage conditions. Stability studies through 14 days were performed in the initial validation studies.

a) High Titer Sera—Human sera exhibiting high titer anti-SARS CoV-2 nAb activity: $ID_{50}$>1:5000 b) Intermediate Titer Sera—Human sera exhibiting intermediate titer anti-SARS CoV-2 nAb activity: 1:5000≥$ID_{50}$≥1:1000 c) Low Titer Sera—Human sera exhibiting low titer anti-SARS CoV-2 nAb activity: $ID_{50}$<1:1000 d) Negative Human Sera—Human sera lacking anti-SARS CoV-2 nAb activity: $ID_{50}$<1:40

Sample Handling

Two replicates of a low titer sample (LTS) and an intermediate titer sample (ITS) were tested following various handling and storage conditions. Two lots of critical reagents (CR) were used for replicate testing. Stability testing included a freshly thawed tube of sample for comparison (Time 0). Sample stability conditions were selected to reflect possible conditions associated with sample collection, shipment and storage prior to performing the assay.

The results of sample stability testing are recorded in FIG. 27. Notable differences in LTS and ITS titers were not observed across the sample storage and handling conditions. The titers of all replicate test results within a given condition varied less than 1.5 fold. The titers for all individual replicates across all conditions varied less than 1.5 fold from the mean of all conditions tested.

Critical Reagent Stability

The in-process stability of critical reagents was assessed by simulating routine sample testing conditions. Critical reagents consist of the SARS CoV-2 Pseudovirus, Specificity Control Pseudovirus and HEK293-ACE2 Target Cells. The performance of two lots of critical reagents was evaluated by comparing test results generated immediately after recovery from storage (Hour 0) versus six hours (Hour 6) at ambient temperature. In-process assessment of critical reagents was performed using low titer serum (LTS) and intermediate titer serum (ITS) specimens.

The results of Critical Reagent Stability testing are summarized in FIG. 28. Notable differences in LTS and ITS titers were not observed between the Hour 0 and Hour 6. The mean titers across all sample storage conditions did not differ by more than 1.4 fold for the LTS and ITS samples.

The results of sample and critical reagent stability and handling testing satisfied the pre-defined assay acceptance criteria:

a) Sample storage conditions (time, temperature, F/T) will be considered acceptable if the average titers of the Low Titer and Intermediate Titer samples do not differ from the corresponding Time 0 titers by ≥3-fold (one serial dilution).

b) Critical reagent storage conditions (time, temperature) will be considered acceptable if the titers of the Low Titer and Intermediate Titer samples do not differ from the corresponding Time 0 titers by ≥3-fold (one serial dilution).

Example 9—Production of Target Cells for SARS CoV-2 Neutralizing Antibody Assay

As described in Example 1 and in FIGS. 1-3, the target cells in the SARS CoV-2 nAb Assay may be produced by expressing ACE2 or both ACE2 and TMPRSS2 transiently through transfection or the target cells may stably express ACE2 or both ACE2 and TMPRSS2. For transient expression, HEK293VL cells were transfected with 0.5 μg/mL ACE2 and 1 μg/mL TMPRSS2 DNA 24 hours before cells were harvested and used in the SARS CoV-2 neutralizing antibody assays (See FIGS. 29 and 30).

Alternative to transiently expressing target cells, the target cells may be a cell line engineered to stably express ACE2 or both ACE2 and TMPRSS2. The 5A10 cell line that stably expresses ACE2 was produced by transfecting HEK293VL cells with 5 μg/mL ACE2 DNA. Hygromycin antibiotic selection was used (at 150 μg/mL) to select for ACE2 expressing cells. The stable ACE2 expressing cell pool was then screened for SARS CoV-2 pseudovirus infectivity and neutralizing antibody efficiency against SARS CoV-2 pseudovirus. A monoclonal cell line was generated from the stable cell pool using limiting dilution and was maintained under 150 μg/mL hygromycin selection. The stable monoclonal ACE2 expressing culture was then screened for SARS CoV-2 pseudovirus infectivity and neutralizing antibody efficiency against SARS CoV-2 pseudovirus (See FIGS. 29 and 30).

The 5G7 cell line that stably expresses both ACE2 and TMPRSS2 was produced by transfecting the 5A10 cell line (ACE2/HEK293VL) with 1 μg/mL TMPRSS2 DNA. Blasticidin antibiotic selection (at 10 μg/mL) was used to select for TMPRSS2 expressing cells, and the cells were maintained under hygromycin selection (at 150 μg/mL) to maintain ACE2 expression. The stable ACE2/TMPRSS2 expressing cell pool was then screened for SARS CoV-2 pseudovirus infectivity and neutralizing antibody efficiency against SARS CoV-2 pseudovirus. A monoclonal cell line was generated from the stable ACE2/TMPRSS2 expressing cell pool using limiting dilution and was maintained under the 10 μg/mL blasticidin and 150 μg/mL hygromycin antibiotic selection. The stable monoclonal ACE2/TMPRSS2 expressing culture was then screened for SARS CoV-2 pseudovirus infectivity and neutralizing antibody efficiency against SARS CoV-2 pseudovirus (See FIGS. 29 and 30).

Figure 29:
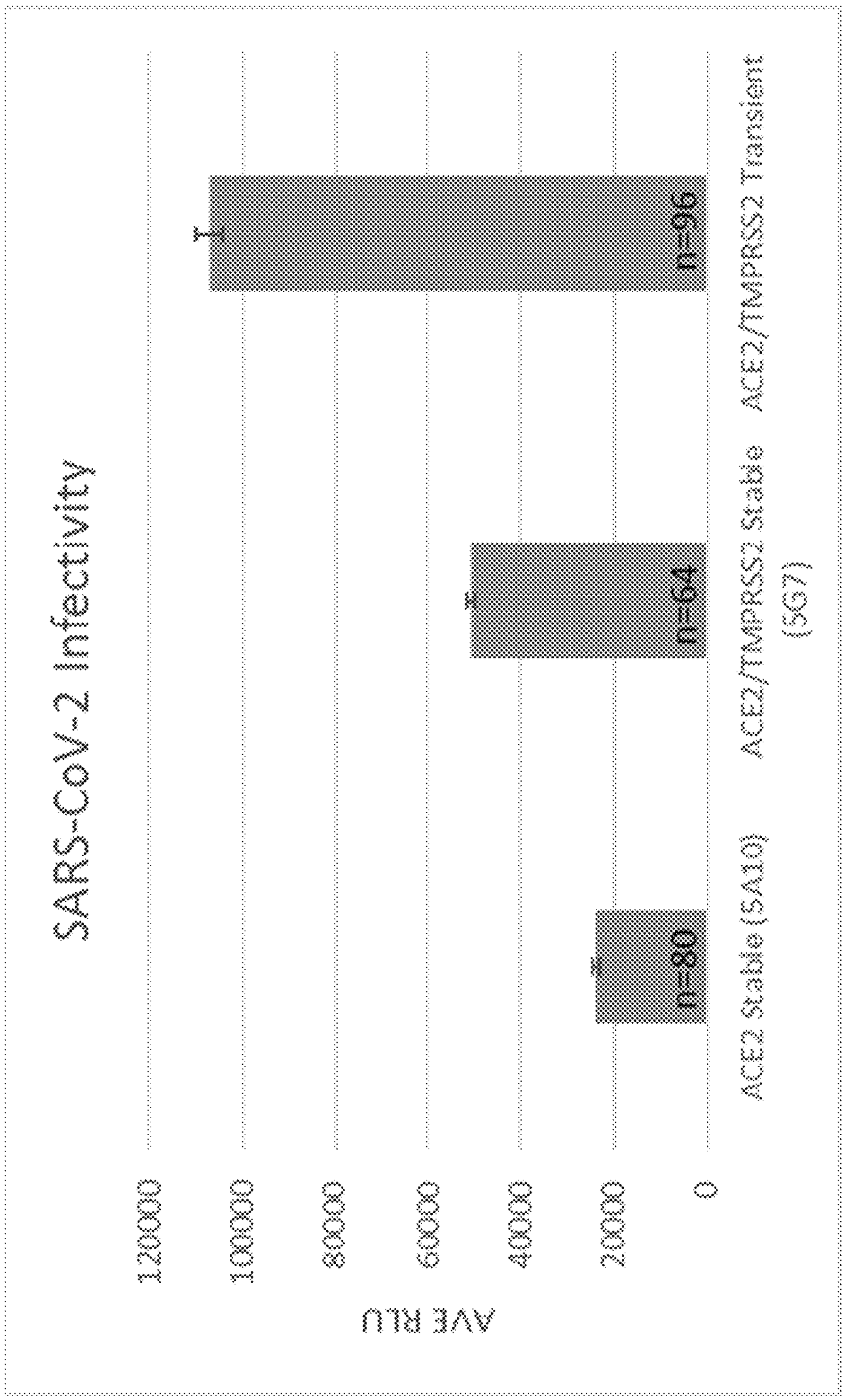
FIG. 29 is a graph showing the infectivity of SARS CoV2 pseudovirus in exemplary assays in which the target cells stably express ACE2 or both ACE2 and TMPRSS2 or in which ACE2 and TMPRSS2 are transiently expressed on the target cells. The target cell type is shown on the x axis, and the average relative luciferase units (RLU) are shown on the y axis.
Figure 30:
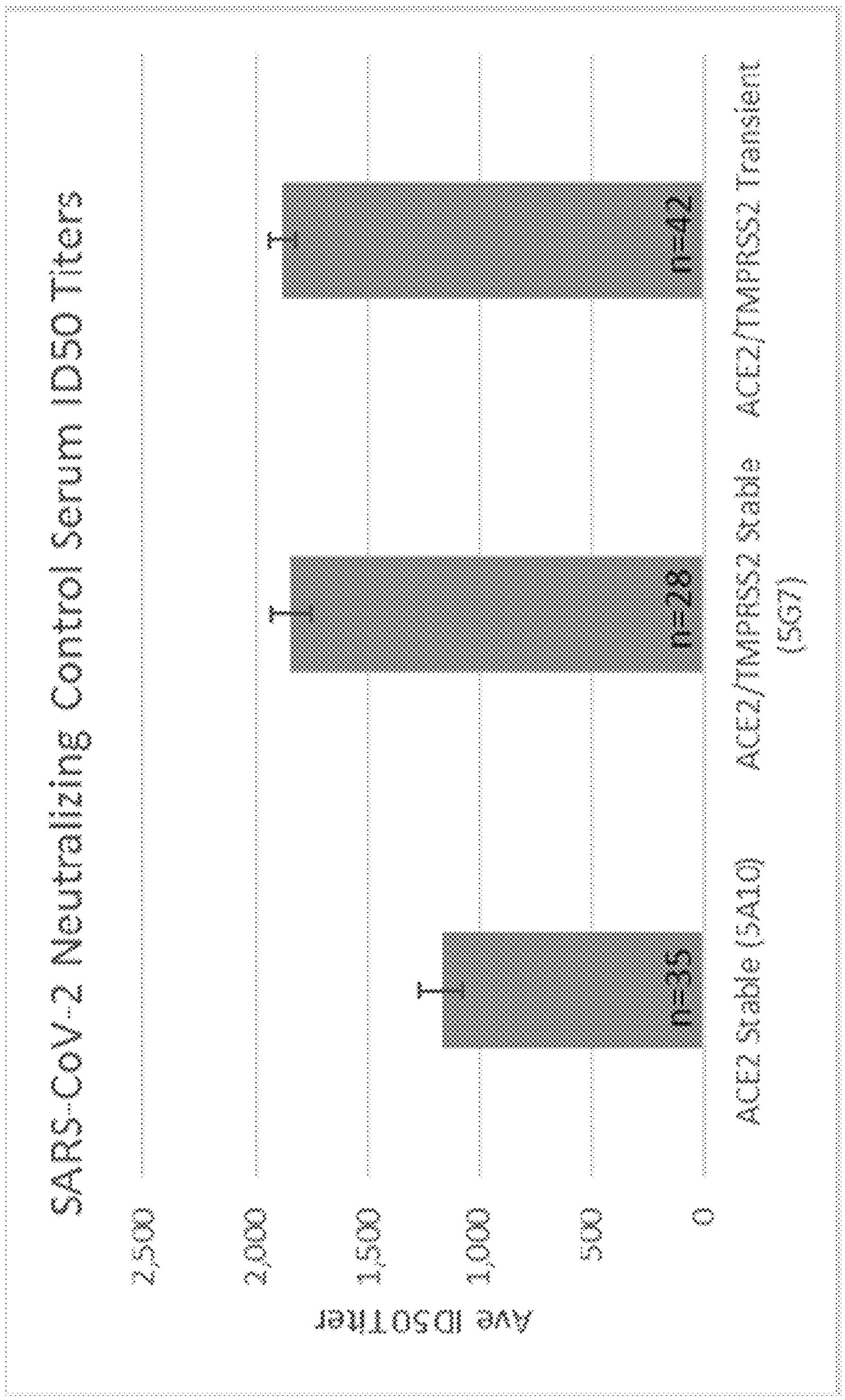
FIG. 30 is a graph showing in exemplary assays the efficiency of neutralizing control serum against the infection of target cells that stably express ACE2 or both ACE2 and TMPRSS2 or in which ACE2 and TMPRSS2 are transiently expressed on the target cells.

The results with these three target cell types for the assays of pseudovirus infectivity and neutralizing antibody efficiency against SARS CoV-2 pseudovirus are shown in FIGS. 29 and 30, respectively. The data in FIG. 29 represent the average infectivity from assays performed with the stably or transiently expressing cells on 4 different days, and the number of pseudoviruses tested with each cell type is indicated. Cells transiently or stably expressing both ACE2 and TMPRSS2 exhibited higher pseudovirus infectivity than cells stably expressing ACE2 alone. The data shown in FIG. 30 represent the average $ID_{50}$ titer of SARS CoV-2 neutralizing antibody control serum from assays performed on 4 different days, and the number of pseudoviruses tested with each cell is indicated.

Figure 31:
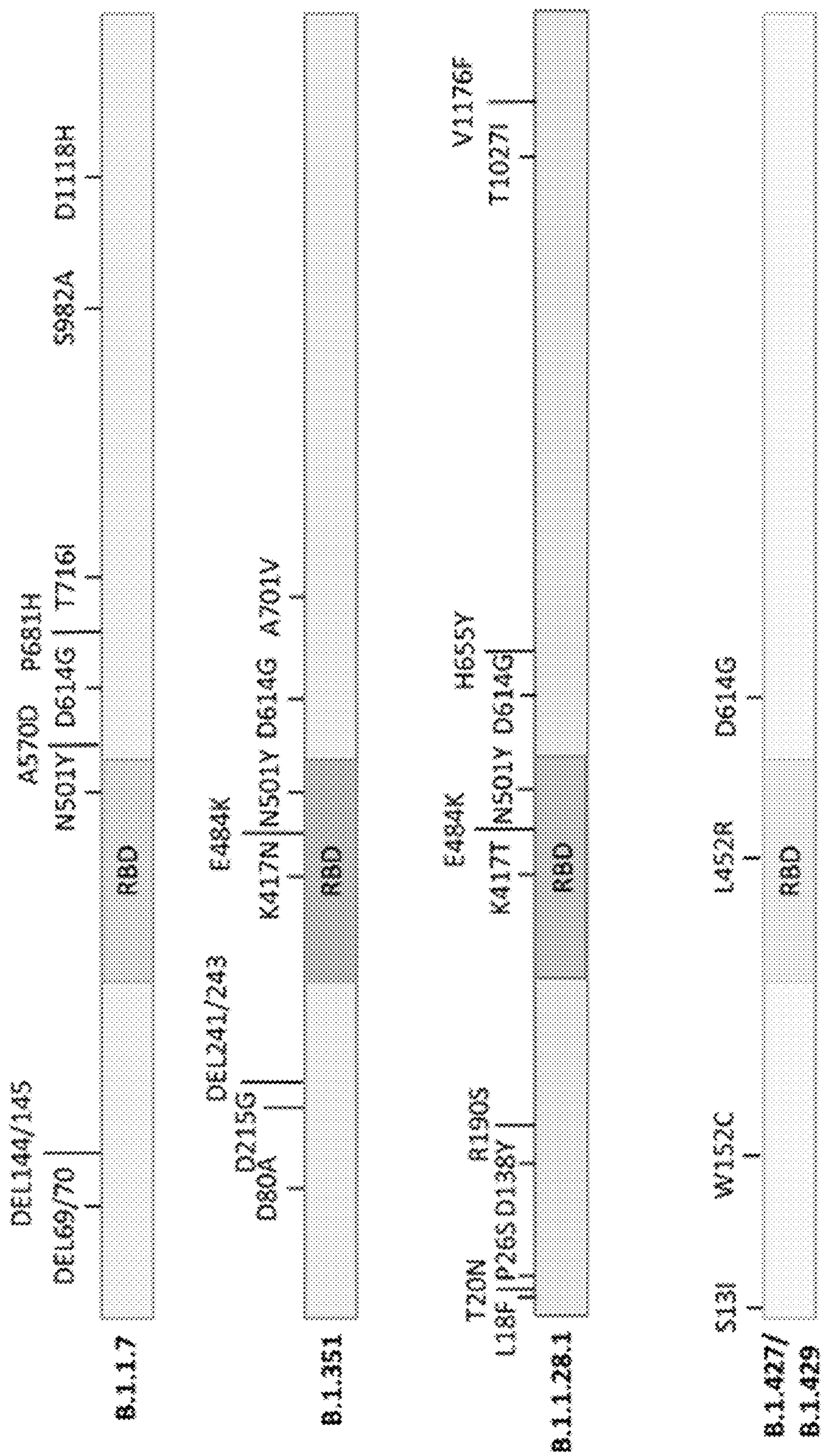
FIG. 31 shows previously identified SARS-CoV-2 variants including B.1.1.7 (UK) variant, B.1.351 (South Africa) variant, B.1.1.28.1 (Brazil) variant, and B.1.427/B.1.429 (California) variant, along with many of the single mutations that have been identified in the S protein of each variant.

Example 10—Detection of Neutralizing Antibody Activity Against SARS-CoV-2 Variants Using a Recombinant HIV Pseudovirus Platform The efficacy of neutralizing antibodies raised against the original SARS-CoV-2 strains (Wuhan) were tested against the latest SARS-CoV-2 variants circulating in the population. The variants studied included B.1.1.7 (UK) variant, B.1.351 (South Africa) variant, B.1.1.28.1 (Brazil) variant, and B.1.427/B.1.429 (California) variant, along with many of the single mutations that are included in each variant, shown in FIG. 31.

As is shown in FIG. 32, infectivity (relative luminescence units; RLU) was determined for each tested variant and single mutant pseudovirus. Results were normalized against Wuhan RLU which was run as a plate control. All single mutant psueudoviruses included the D614G mutation. The relative infectivity of each pseudovirus in our in vitro assay provides insight about the transmissibility of each variant in the population and which mutations contribute to increased infectivity.

Figure 35:
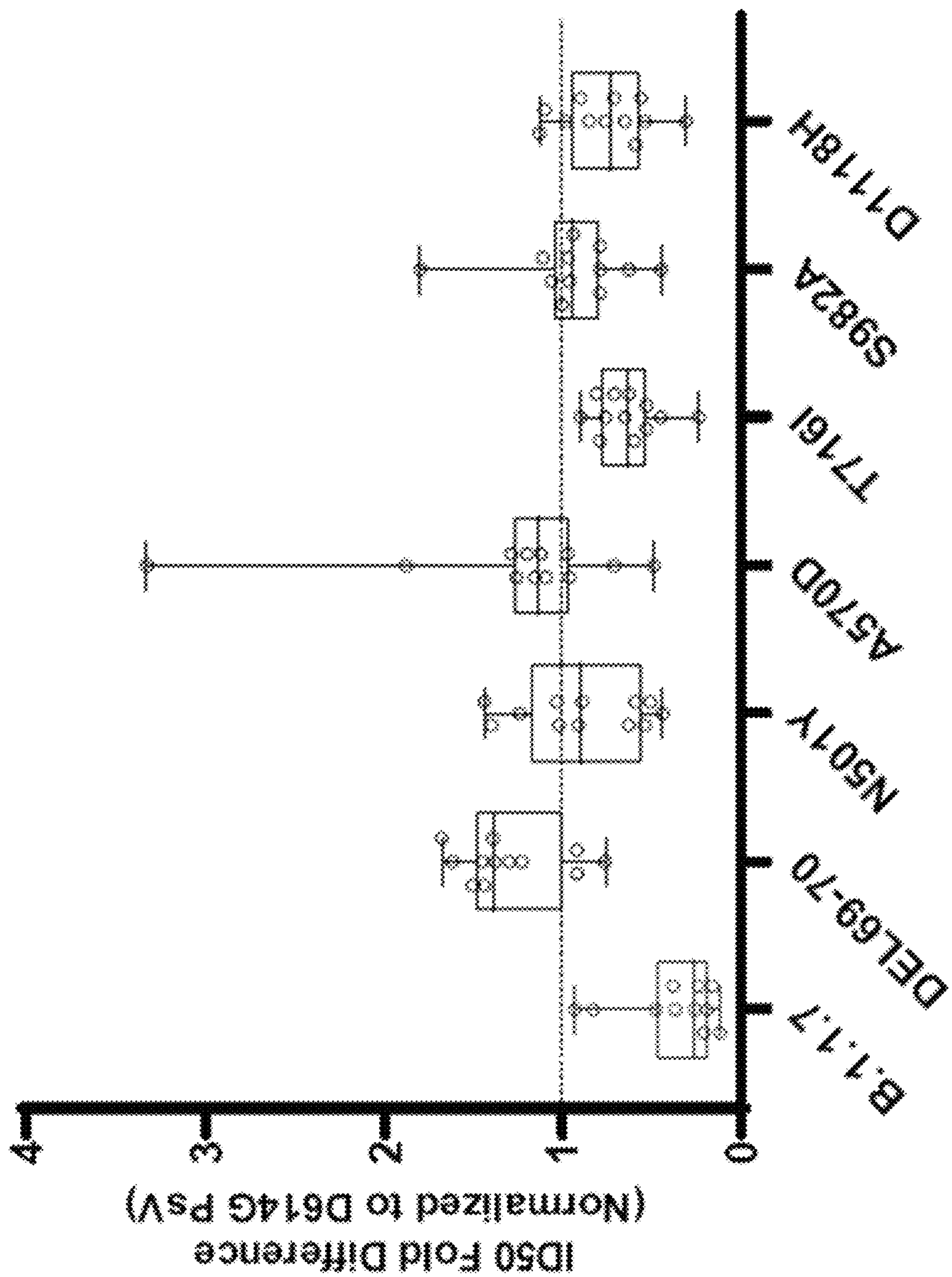
FIG. 35 shows box and whisker plots of the ID50 fold difference for the B.1.1.7 variant pseudovirions (PsV) and PsV having individual mutations characteristic of B.1.1.7 as compared to D614G SAR-CoV-2 PsV, where the box indicates the interquartile range, the midline of each box indicates the median, and the arms indicate the maximum and minimum in accordance with an embodiment of the disclosure.
Figure 36:
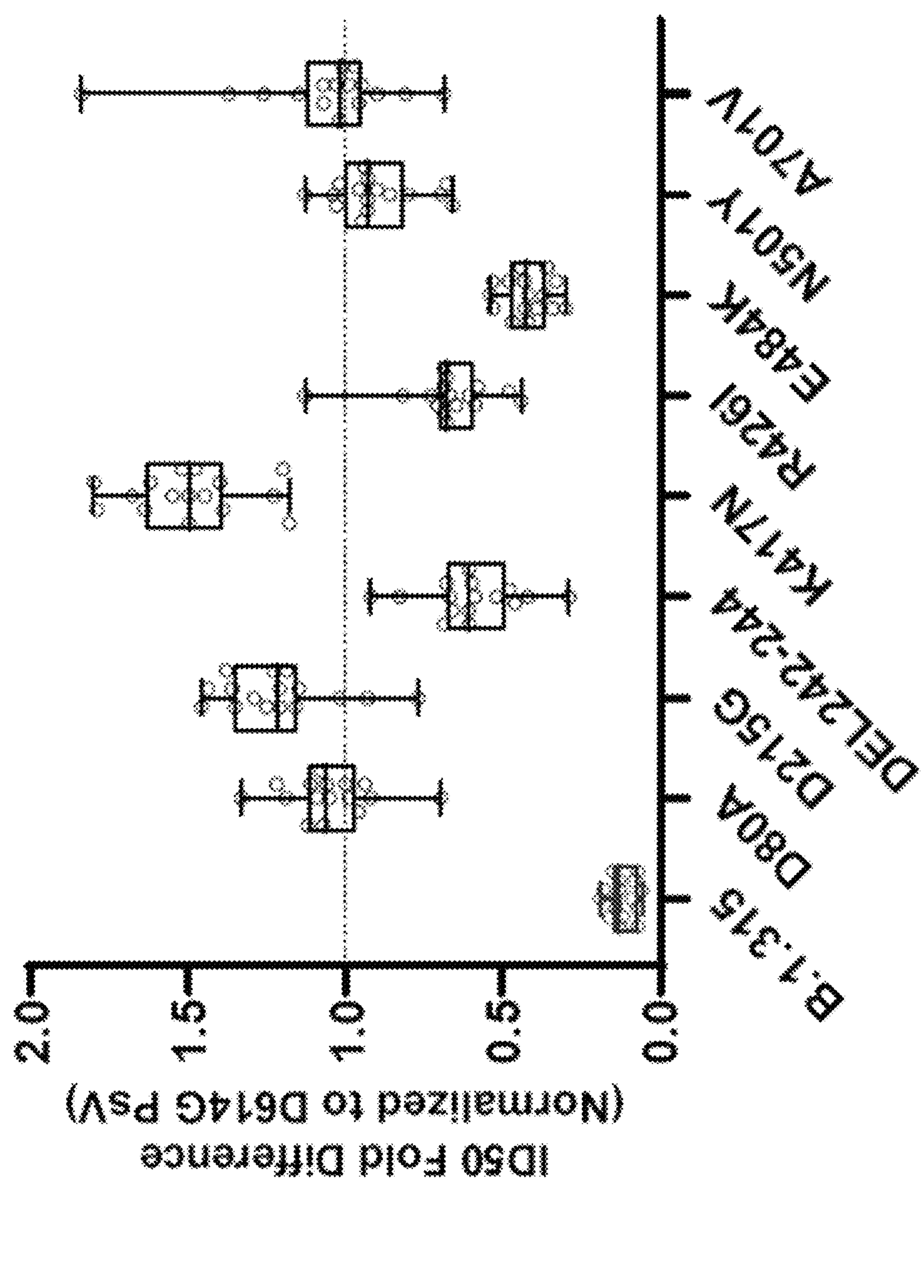
FIG. 36 shows a box and whisker plots of the ID50 fold difference for B.1.351 variant pseudovirions (PsV) and PsV having individual mutations characteristic of B.1.351 as compared to D614G PsV, where the box indicates the interquartile range, the midline of each box indicates the median, and the arms indicate the maximum and minimum in accordance with an embodiment of the disclosure.

Pseudoviruses were also tested against a panel of 12 sera pools known to neutralize SARS-CoV-2 (Wuhan or D614G) pseudoviruses. Sera pools were generated by mixing 8-16 samples of similar titer. FIG. 33 shows an example (B1.1.7) ID50 table displaying neutralization titers for each sample generated from a 10-point sample titration curve. FIG. 34 shows the fold difference of each sample (B.1.1.7) titer for each pseudovirus normalized using D614G SARS-CoV-2 pseudovirus, along with each's mean and median. FIG. 35 and FIG. 36 show box and whisker plots generated for each pseudovirus where the box indicates the interquartile range, the midline of each box indicates the median, and the arms indicate the maximum and minimum. The fold difference of each sera pool ID50 point is also plotted. The pseudovirus variants of concern (B.1.1.7 and B.1.351) are plotted first. All single mutant pseudoviruses also include the D614G mutation.

No single mutation was fully responsible for the nAB escape capability of B.1.1.7 or B.1.351. In this assay, the N501Y variant had little to no enhanced nAb escape capability. The mutations that contributed to B.1.1.7 nAb escape capability in the assay were T716I and/or D1118H. The mutations that contributed to B.1.351 nAb escape capability were DEL242-244, R426I, and E484K. However, each of these nAb escape contributing mutations showed lower infectivity compared to other pseudoviruses.

Example 11—Examples of Certain Embodiments

Listed hereafter are non-limiting examples of certain embodiments of the technology.

A1. A method for detecting whether a subject exposed to a coronavirus has developed a neutralizing antibody response, comprising:

(a) transfecting into a plurality of first cells:

i) a nucleic acid encoding a coronavirus spike protein, and ii) a viral expression vector which comprises an indicator nucleic acid which produces a detectable signal;

(b) incubating the first cells under conditions such that the first cells produce viral particles comprising the coronavirus spike protein;

(c) contacting the viral particles of step (b) with a second cell in the presence or absence of a sample comprising an antibody from the subject, wherein the second cell expresses a cell surface receptor to which the coronavirus binds;

(d) measuring the amount of the detectable signal produced by the second cell in order to determine the infectivity of the viral particles in the presence or absence of the sample; and (e) comparing the amount of signal measured in step (d) in the presence of the sample with the amount of signal produced in step (d) in the absence of the sample, wherein a reduced amount of signal measured in the presence of the sample indicates that the subject has developed a neutralizing antibody response capable of reducing infection.

A2. The method of embodiment A1, wherein the antibody response is a neutralizing antibody response that inhibits infection in a therapeutically effective manner.

A3. The method of embodiment A1, wherein the coronavirus spike protein is a coronavirus S protein.

A4. The method of embodiment A1, wherein the indicator nucleic acid comprises an indicator gene.

A5. The method of embodiment A4, wherein the indicator gene is a luciferase gene.

A6. The method of embodiment A1, wherein the cell surface receptor is ACE-2.

A7. The method of embodiment A1, wherein the subject was infected with a coronavirus.

A8. The method of embodiment A1, wherein the subject was infected with severe acute respiratory syndrome coronavirus 2 (SARS CoV-2).

A9. The method of embodiment A1, wherein the first cells are mammalian cells.

A10. The method of embodiment A1, wherein the first cells are human cells.

A11. The method of embodiment A1, wherein the first cells are human embryonic kidney cells.

A12. The method of embodiment A11, wherein the human embryonic kidney cells are 293 cells.

A13. The method of embodiment A1, wherein the second cell is a mammalian cell.

A14. The method of embodiment A1, wherein the second cell is a human cell.

A15. The method of embodiment A1, wherein the second cell is a human embryonic kidney cell.

A16. The method of embodiment A15, wherein the human embryonic kidney cell is a 293 cell.

A17. The method of embodiment A1, wherein the sample is serum or plasma.

A18. The method of embodiment A1, wherein the viral expression vector is a human immunodeficiency virus (HIV) expression vector.

A19. The method of embodiment A6, wherein the second cell further expresses human airway transmembrane trypsin-like serine protease (TMPRSS2).

A20. The method of embodiment A19, wherein ACE-2, TMPRSS2, or both are stably expressed by the second cell.

A21. The method of embodiment A1, wherein the level of neutralizing antibody response in the sample is correlated to a titer of total anti-coronavirus antibody as measured for the subject.

B1. A method for determining whether a first subject infected by a virus is likely to respond to treatment with an antibody preparation, comprising:

(a) transfecting into a plurality of first cells
   i) a nucleic acid encoding a coronavirus spike protein from the subject, and
   ii) a viral expression vector which comprises an indicator nucleic acid which produces a detectable signal;

(b) incubating the first cells under conditions such that the first cells produce viral particles comprising the coronavirus spike protein;

(c) contacting the viral particles of step (b) with a second cell in the presence or absence of the antibody preparation, wherein the second cell expresses a cell surface receptor to which the virus binds;

(d) measuring the amount of the detectable signal produced by the second cell in order to determine the infectivity of the viral particles in the presence or absence of the antibody preparation; and (e) comparing the amount of signal measured in step (d) in the presence of the antibody preparation with the amount of signal produced in step (d) in the absence of the antibody preparation, wherein a reduced amount of signal measured in the presence of the antibody preparation from the second subject indicates that the subject is likely to be responsive to treatment with the antibody preparation.

B2. The method of embodiment B1, wherein the antibody preparation is from a second subject.

B3. The method of embodiment B1, wherein the antibody preparation is produced in cell culture.

B4. The method of embodiment B1, wherein the antibody response is a neutralizing antibody response that inhibits infection in a therapeutically effective manner.

B5. The method of embodiment B1, wherein the coronavirus spike protein is a coronavirus S protein.

B6. The method of embodiment B1, wherein the indicator nucleic acid comprises an indicator gene.

B7. The method of embodiment B4, wherein the indicator gene is a luciferase gene.

B8. The method of embodiment B1, wherein the cell surface receptor is ACE-2.

B9. The method of embodiment B2, wherein the second subject was infected with a coronavirus.

B10. The method of embodiment B2, wherein the second subject was infected with severe acute respiratory syndrome coronavirus 2 (SARS CoV-2).

B11. The method of embodiment B1, wherein the first cells are mammalian cells.

B12. The method of embodiment B1, wherein the first cells are human cells.

B13. The method of embodiment B1, wherein the first cells are human embryonic kidney cells.

B14. The method of embodiment B13, wherein the human embryonic kidney cells are 293 cells.

B15. The method of embodiment B1, wherein the second cell is a mammalian cell.

B16. The method of embodiment B1, wherein the second cell is a human cell.

B17. The method of embodiment B1, wherein the second cell is a human embryonic kidney cell.

B18. The method of embodiment B17, wherein the human embryonic kidney cell is a 293 cell.

B19. The method of embodiment B1, wherein the sample is serum or plasma.

B20. The method of embodiment B1, wherein the viral expression vector is a human immunodeficiency virus (HIV) expression vector.

B21. The method of embodiment B8, wherein the second cell further expresses human airway transmembrane trypsin-like serine protease (TMPRSS2).

B22. The method of embodiment B21, wherein ACE-2, TMPRSS2, or both are stably expressed by the second cell.

C.1.1. A method for detecting the level of neutralizing antibody response in a sample from a subject exposed to a coronavirus comprising:

(a) transfecting into a plurality of first cells:
  i) a nucleic acid encoding a coronavirus spike protein, and
  ii) a viral expression vector which comprises an indicator nucleic acid which produces a detectable signal;

(b) incubating the first cells under conditions such that the first cells produce viral particles comprising the coronavirus spike protein;

(c) contacting the viral particles of step (b) with a second cell in the presence or absence of a sample from the subject that was exposed to a coronavirus, wherein the second cell expresses a cell surface receptor to which the coronavirus binds;

(d) measuring the amount of the detectable signal produced by the second cell in order to determine the infectivity of the viral particles in the presence or absence of the sample; and (e) comparing the amount of signal measured in step (d) in the presence of the sample with the amount of signal produced in step (d) in the absence of the sample, and;

(f) determining the level of a neutralizing antibody response in the sample based on the extent of the reduction in infectivity of the viral particles exposed to the sample as compared to the infectivity of the viral particles not exposed to the sample.

C.1.2. The method of embodiment C.1.1, wherein the antibody response is a neutralizing antibody response that inhibits infection in a therapeutically effective manner.

C.1.3. The method of embodiment C.1.1, wherein the coronavirus envelope spike is a coronavirus S protein.

C.1.4. The method of embodiment C.1.1, wherein the indicator nucleic acid comprises an indicator gene.

C.1.5. The method of embodiment C.1.4, wherein the indicator gene is a luciferase gene.

C.1.6. The method of embodiment C.1.1, wherein the cell surface receptor is ACE-2.

C.1.7. The method of embodiment C.1.1, wherein the subject was infected with a coronavirus.

C.1.8. The method of embodiment C.1.1, wherein the subject was infected with severe acute respiratory syndrome coronavirus 2 (SARS CoV-2).

C.1.9. The method of embodiment C.1.1, wherein the first cells are mammalian cells.

C.1.10. The method of embodiment C.1.1, wherein the first cells are human cells.

C.1.11. The method of embodiment C.1.1, wherein the first cells are human embryonic kidney cells.

C.1.12. The method of embodiment C.1.11, wherein the human embryonic kidney cells are 293 cells.

C.1.13. The method of embodiment C.1.1, wherein the second cell is a mammalian cell.

C.1.14. The method of embodiment C.1.1, wherein the second cell is a human cell.

C.1.15. The method of embodiment C.1.1, wherein the second cell is a human embryonic kidney cell.

C.1.16. The method of embodiment C.1.15, wherein the human embryonic kidney cell is a 293 cell.

C.1.17. The method of embodiment C.1.1, wherein the viral expression vector is a human immunodeficiency virus (HIV) expression vector.

C.1.18. The method of embodiment C.1.6, wherein the second cell further expresses human airway transmembrane trypsin-like serine protease (TMPRSS2).

C.1.19. The method of embodiment C.1.18, wherein ACE-2, TMPRSS2, or both are stably expressed by the second cell.

C.1.20. The method of embodiment C.1.1, wherein the sample is a serum sample.

C.1.21. The method of embodiment C.1.1, wherein the level of neutralizing antibody response of the sample is correlated to the subject's level of post-infection protective immunity.

C.1.22. The method of embodiment C.1.1, wherein the level of neutralizing antibody response in the sample is correlated to a titer of total anti-coronavirus antibody as measured for the subject.

C.2.1. A method for detecting the level of neutralizing antibody response in a sample from a subject exposed to a coronavirus vaccine comprising:

(a) transfecting into a plurality of first cells:
  i) a nucleic acid encoding a coronavirus spike protein, and
  ii) a viral expression vector which comprises an indicator nucleic acid which produces a detectable signal;

(b) incubating the first cells under conditions such that the first cells produce viral particles comprising the coronavirus spike protein;

(c) contacting the viral particles of step (b) with a second cell in the presence of a sample from the subject obtained before the subject was exposed to a coronavirus vaccine or a sample from the subject obtained after the subject was exposed to a coronavirus vaccine, wherein the second cell expresses a cell surface receptor to which the coronavirus binds;

(d) measuring the amount of the detectable signal produced by the second cell in the presence of the sample obtained before the subject was exposed to the coronavirus vaccine;

(e) measuring the amount of the detectable signal produced by the second cell in the presence of the sample obtained after the subject was exposed to the coronavirus vaccine; and (f) comparing the amount of signal measured in step (d) with the amount of signal produced in step (e), and determining the level of a neutralizing antibody response in the subject based on the difference in the amount of signal measured in step (d) with the amount of signal produced in step (e).

C.2.2. The method of embodiment C.2.1, wherein the antibody response is a neutralizing antibody response that inhibits infection in a therapeutically effective manner.

C.2.3. The method of embodiment C.2.1, wherein the coronavirus spike protein is a coronavirus S protein.

C.2.4. The method of embodiment C.2.1, wherein the indicator nucleic acid comprises an indicator gene.

C.2.5. The method of embodiment C.2.4, wherein the indicator gene is a luciferase gene.

C.2.6. The method of embodiment C.2.1, wherein the cell surface receptor is ACE-2.

C.2.7. The method of embodiment C.2.1, wherein the first cells are mammalian cells.

C.2.8. The method of embodiment C.2.1, wherein the first cells are human cells.

C.2.9. The method of embodiment C.2.1, wherein the first cells are human embryonic kidney cells.

C.2.10. The method of embodiment C.2.9, wherein the human embryonic kidney cells are 293 cells.

C.2.11. The method of embodiment C.2.1, wherein the second cell is a mammalian cell.

C.2.12. The method of embodiment C.2.1, wherein the second cell is a human cell.

C.2.13. The method of embodiment C.2.1, wherein the second cell is a human embryonic kidney cell.

C.2.14. The method of embodiment C.2.13, wherein the human embryonic kidney cell is a 293 cell.

C.2.15. The method of embodiment C.2.1, wherein the viral expression vector is a human immunodeficiency virus (HIV) expression vector.

C.2.16. The method of embodiment C.2.6, wherein the second cell further expresses human airway transmembrane trypsin-like serine protease (TMPRSS2).

C.2.17. The method of embodiment C.2.16, wherein ACE-2, TMPRSS2, or both are stably expressed by the second cell.

C.2.18. The method of embodiment C.2.1, wherein the sample is a serum sample.

C.2.19. The method of embodiment C.2.1, wherein the level of neutralizing antibody response of the sample is correlated to the subject's level of post-vaccination protective immunity.

C.2.20. The method of embodiment C.2.1, wherein the level of neutralizing antibody response in the sample is correlated to a titer of total anti-coronavirus antibody as measured for the subject.

D.1.1 A method for evaluating a mutation in the SARS CoV-2 spike protein on susceptibility to an anti-SARS CoV-2 antibody comprising:

- (a) transfecting into a first portion of a plurality of first cells:
  - i) a nucleic acid encoding a control coronavirus spike protein, and
  - ii) a viral expression vector which comprises an indicator nucleic acid which produces a detectable signal;
- (b) transfecting into a second portion of a plurality of first cells:
  - i) a nucleic acid encoding a coronavirus spike protein that comprises a mutation; and
  - ii) a viral expression vector which comprises an indicator nucleic acid which produces a detectable signal;
- (c) incubating the first and second portion of first cells separately under conditions such that the first portion cells produce first viral particles comprising the control coronavirus spike protein, and the second portion cells produce second viral particles comprising the coronavirus spike protein having the mutation;
- (d) contacting the first viral particles of step (c) with a first portion of a plurality of second cells in the presence of a sample comprising an antibody that binds SARS CoV-2, wherein the second cell expresses a cell surface receptor to which the coronavirus binds;
- (e) contacting the second viral particles of step (c) with a second portion of a plurality of second cells in the presence of a sample comprising an antibody that binds SARS CoV-2, wherein the second cell expresses a cell surface receptor to which the coronavirus binds; and
- (f) measuring the amount of the detectable signal produced by the second cell in steps (d) and (e), wherein a reduced amount of signal produced by the second cell in step (d) as compared to the signal produced by the second cell in step (e) indicates that the mutation in the spike protein confers a reduced susceptibility of the viral particles to the anti-SARS CoV-2 antibody.

D.1.2. The method of embodiment D.1.1, wherein the control coronavirus spike protein is from a wild type coronavirus or is obtained from the same subject at a different time point.

D.1.3. The method of embodiment D.1.1, wherein the antibody response is a neutralizing antibody response that inhibits infection in a therapeutically effective manner.

D.1.4. The method of embodiment D.1.1, wherein the coronavirus envelope spike is a coronavirus S protein.

D.1.5. The method of embodiment D.1.1, wherein the indicator nucleic acid comprises an indicator gene.

D.16. The method of embodiment D.1.5, wherein the indicator gene is a luciferase gene.

D.17. The method of embodiment D.1.1, wherein the cell surface receptor is ACE-2.

D1.8. The method of embodiment D.1.1, wherein the subject was infected with a coronavirus.

D.1.9. The method of embodiment D1.1, wherein the subject was infected with severe acute respiratory syndrome coronavirus 2 (SARS CoV-2).

D.1.10. The method of embodiment D.1.1, wherein the first cells are mammalian cells.

D.1.11. The method of embodiment D.1.1, wherein the first cells are human cells.

D.1.12. The method of embodiment D.1.1, wherein the first cells are human embryonic kidney cells.

D.1.13. The method of embodiment D.1.11, wherein the human embryonic kidney cells are 293 cells.

D.1.14. The method of embodiment D.1.1, wherein the second cell is a mammalian cell.

D.1.15. The method of embodiment D.1.1, wherein the second cell is a human cell.

D.1.16. The method of embodiment D.1.1, wherein the second cell is a human embryonic kidney cell.

D.1.17. The method of embodiment D.1.16, wherein the human embryonic kidney cell is a 293 cell.

D.1.18. The method of embodiment D.1.1, wherein the viral expression vector is a human immunodeficiency virus (HIV) expression vector.

D.1.19. The method of embodiment D.1.6, wherein the second cell further expresses human airway transmembrane trypsin-like serine protease (TMPRSS2).

D.1.20. The method of D.1.19, wherein ACE-2, TMPRSS2, or both are stably expressed by the second cell.

D.1.21. The method of embodiment D.1.1, wherein the antibody response is a neutralizing antibody response, and the titer of the neutralizing antibody response is correlated to protective immunity.

D.1.22. The method of embodiment D.1.1, wherein the variant is one of the B.1.1.7, B.351, B.1.1.28.1 or B.1.427/1.429 variants.

D.1.23 The method of embodiment D.1.1, the mutated spike protein is isolated from a subject exposed to coronavirus.

D.1.24 The method of embodiment D.1.1, wherein the spike protein is genetically modified in vitro.

D.2.1 A method for detecting the level of neutralizing antibody response to a mutated or variant SARS-CoV-2 in a subject previously exposed to a coronavirus vaccine comprising:

- (a) transfecting into a plurality of first cells: i) a nucleic acid encoding a coronavirus spike protein (i.e., the variant spike protein), and ii) a viral expression vector which comprises an indicator nucleic acid which produces a detectable signal;

(b) incubating the first cells under conditions such that the first cells produce viral particles comprising the mutant/variant coronavirus spike protein;
(c) contacting the viral particles of step (b) separately with i) a second cell in the presence of a sample obtained from the subject before the subject was exposed to a coronavirus vaccine; and ii) a second cell in the presence of a sample from the subject obtained after the sample was exposed to the coronavirus vaccine, wherein the second cell expresses a cell surface receptor to which the coronavirus binds;
(d) measuring the amount of the detectable signal produced by the second cell in order to determine the infectivity of the viral particles in the presence of the sample obtained before the subject was exposed to the coronavirus vaccine; and
(e) measuring the amount of the detectable signal produced by the second cell in order to determine the infectivity of the viral particles in the presence of the sample obtained after the subject was exposed to the coronavirus vaccine; and
(f) comparing the amount of signal measured in step (d) with the amount of signal produced in step (e), and determining the level of a neutralizing antibody response in the sample based on the difference in the amount of signal measured in step (d) with the amount of signal produced in step (e).

D.2.2. The method of embodiment D.2.1, wherein the antibody response is a neutralizing antibody response that inhibits infection in a therapeutically effective manner.

D.2.3. The method of embodiment D.2.1, wherein the coronavirus spike protein is a coronavirus S protein.

D.2.4. The method of embodiment D.2.1, wherein the indicator nucleic acid comprises an indicator gene.

D.2.5. The method of embodiment D.2.4, wherein the indicator gene is a luciferase gene.

D.2.6. The method of embodiment D.2.1, wherein the cell surface receptor is ACE-2.

D2.7. The method of embodiment D.2.1, wherein the first cells are mammalian cells.

D.2.8. The method of embodiment D.2.1, wherein the first cells are human cells.

D.2.9. The method of embodiment D.2.1, wherein the first cells are human embryonic kidney cells.

D2.10. The method of embodiment D.2.9, wherein the human embryonic kidney cells are 293 cells.

D.2.11. The method of embodiment D.2.1, wherein the second cell is a mammalian cell.

D.2.12. The method of embodiment D.2.1, wherein the second cell is a human cell.

D.2.13. The method of embodiment D.2.1, wherein the second cell is a human embryonic kidney cell.

D.2.14. The method of embodiment D.2.13, wherein the human embryonic kidney cell is a 293 cell.

D.2.15. The method of embodiment D.2.1, wherein the viral expression vector is a human immunodeficiency virus (HIV) expression vector.

D.2.16. The method of embodiment D.2.6, wherein the second cell further expresses human airway transmembrane trypsin-like serine protease (TMPRSS2).

D.2.17. The method of embodiment D.2.16, wherein ACE-2, TMPRSS2, or both are stably expressed by the second cell.

D.2.18. The method of embodiment D.2.1, wherein the sample is a serum sample.

D.2.19. The method of embodiment D.2.1, wherein the level of neutralizing antibody response of the sample is correlated to the subject's level of post-vaccination protective immunity.

D.2.20. The method of embodiment D.2.1, wherein the level of neutralizing antibody response in the sample is correlated to a titer of total anti-coronavirus antibody as measured for the subject.

D.2.21. The method of embodiment D.2.1, wherein the variant is one of the B.1.1.7, B.351, B.1.1.28.1 or B.1.427/1.429 variants.

D.2.22 The method of embodiment D.2.1, the spike protein of step (a) is isolated from the subject.

D.2.23 The method of embodiment D.2.1, wherein the spike protein is genetically modified in vitro.

D.2.24 The method of embodiment D.2.1, wherein the results with the mutated spike protein are compared to a normal (i.e., non-mutated) spike protein control.

E1. The method of any of the preceding embodiments, wherein the second cell transiently expresses ACE-2.

E2. The method of any of the preceding embodiments, wherein the second cell stably expresses ACE-2.

E3. The method of any of the preceding embodiments, wherein the second cell transiently expresses TMPRSS2.

E4. The method of any of the preceding embodiments, wherein the second cell stably expresses TMPRSS2.

E5. The method of any of the preceding embodiments, wherein the coronavirus spike protein comprises a mutation.

E6. The method of any of the preceding embodiments, wherein the coronavirus spike protein comprises a mutation that increases viral infectivity.

E7. The method of any of the preceding embodiments, wherein the coronavirus spike protein comprises a D614G mutation.

E8. The method of any of the preceding embodiments, wherein the second cell expresses low levels of ACE-2.

E9. The method of any of the preceding embodiments, wherein the second cell expresses normal levels of ACE-2.

E10. The method of any of the preceding embodiments, wherein the second cell expresses high levels of ACE-2.

F1. A system comprising a station and/or genetically modified cells for performing any of the steps of any of the previous embodiments or use of any one of the compositions of any of the subsequent embodiments.

G1. A computer-program product tangibly embodied in a non-transitory machine-readable storage medium, including instructions configured to perform any of the steps of the methods of any of the previous embodiments, or use any one of the compositions of any of the subsequent embodiments, or run any part of the system of embodiment F1.

H1. A composition for the detection of a compound that can modulate SARS infectivity.

H2. The composition of G1, comprising a cell that has been genetically modified to be either a producer cell or a target cell.

H3. The composition of any one of the previous or subsequent embodiments, comprising a first cell that has been genetically modified to be a target cell that expresses an angiotensin-converting enzyme 2 receptor (ACE-2).

H4. The composition of any one of the previous or subsequent embodiments, wherein the target cell is genetically modified to also express human airway transmembrane trypsin-like serine protease (TMPRSS2).

H5. The composition of any one of the previous or subsequent embodiments comprising a producer cell.

H6. The composition of any one of the previous or subsequent embodiments, wherein the producer cell is a genetically modified second cell that expresses: i) a SARS CoV-2 spike protein or a portion thereof, and ii) a second virus, or a portion thereof, that is not a coronavirus and that comprises an indicator nucleic acid that produces a detectable signal.

H7. The composition of any one of the previous or subsequent embodiments, wherein the producer cell generates pseudovirions that comprise the SARS CoV-2 spike protein or a portion thereof.

H8. The composition of any one of the previous or subsequent embodiments, wherein the coronavirus spike protein is a coronavirus S protein.

H9. The composition of any one of the previous or subsequent embodiments, wherein the S protein is from a subject infected with a coronavirus.

H10. The composition of any one of the previous or subsequent embodiments, wherein the subject is infected with severe acute respiratory syndrome coronavirus 2 (SARS CoV-2).

H11. The composition of any one of the previous or subsequent embodiments, wherein the second virus is HIV or a genetically modified HIV.

H12. The composition of any one of the previous or subsequent embodiments, wherein the indicator nucleic acid comprises an indicator gene.

H13. The composition of any one of the previous or subsequent embodiments, wherein the indicator gene is a luciferase gene.

H14. The composition of any one of the previous or subsequent embodiments, wherein the producer cells and/or the target cells are mammalian cells.

H15. The composition of any one of the previous or subsequent embodiments, wherein the producer cells and/or the target cells are human cells.

H16. The composition of any one of the previous or subsequent embodiments, wherein the producer cells and/or the target cells are human embryonic kidney (HEK) cells.

H17. The composition of any one of the previous or subsequent embodiments, wherein the human embryonic kidney cells are HEK 293 cells.

H18. The composition of any one of the previous embodiments, wherein the ACE2 and/or TMPRSS2 is introduced into the target cell in a manner that allows for transient expression.

H19. The composition of any one of the previous embodiments, wherein the ACE2 and/or TMPRSS2 is introduced into the target cell in a manner that allows for stable expression.

I1. A kit for performing any of the steps of any of the previous embodiments.

That which is claimed is:

1. A composition comprising a cell that has been genetically modified to be a target cell, wherein the target cell expresses an angiotensin-converting enzyme 2 receptor (ACE-2) and a human airway transmembrane trypsin-like serine protease (TMPRSS2), and wherein the target cell is a human kidney cell.

2. The composition of claim 1, wherein the target cell expresses ACE-2 and TMPRSS2 in a stable manner.

3. The composition of claim 1, wherein the target cell transiently expresses ACE-2 and TMPRSS2.

4. A method for detecting a level of neutralizing antibody response in a sample from a subject exposed to a coronavirus vaccine, comprising:

(a) transfecting into a plurality of first cells:

i) a nucleic acid encoding a coronavirus spike protein, and ii) a viral expression vector which comprises an indicator nucleic acid which produces a detectable signal;

(b) incubating the first cells under conditions such that the first cells produce viral particles comprising the coronavirus spike protein;

(c) contacting the viral particles of step (b) with the composition of claim 1 in the presence of a sample from the subject obtained before the subject was exposed to a coronavirus vaccine or a sample from the subject obtained after the subject was exposed to a coronavirus vaccine;

(d) measuring an amount of the detectable signal produced by the target cell in the presence of the sample obtained before the subject was exposed to the coronavirus vaccine;

(e) measuring an amount of the detectable signal produced by the target cell in the presence of the sample obtained after the subject was exposed to the coronavirus vaccine; and (f) comparing the amount of signal measured in step (d) with the amount of signal produced in step (e), and determining the level of a neutralizing antibody response in the subject based on a difference in the amount of signal measured in step (d) with the amount of signal produced in step (e).

5. The composition of claim 1, wherein the target cell is selected from a group consisting of a 293 cell, a 5A10 cell, and a 5G7 cell.

6. A method for detecting whether a subject exposed to a coronavirus has developed a neutralizing antibody response, comprising:

(a) transfecting into a plurality of first cells i) a nucleic acid encoding a coronavirus spike protein, and ii) a viral expression vector which comprises an indicator nucleic acid which produces a detectable signal;

(b) incubating the first cells under conditions such that the first cells produce viral particles comprising the coronavirus spike protein;

(c) contacting the viral particles of step (b) with the composition of claim 1 in the presence or absence of a sample comprising an antibody from the subject;

(d) measuring an amount of the detectable signal produced by the target cell in the presence or absence of the sample; and (e) comparing the amount of signal measured in step (d) in the presence of the sample with the amount of signal produced in step (d) in the absence of the sample, wherein a reduced amount of signal measured in the presence of the sample indicates that the subject has developed a neutralizing antibody response capable of reducing infection.

7. The method of claim 6, wherein the indicator nucleic acid comprises an indicator gene.

8. The method of claim 7, wherein the indicator gene is a luciferase gene.

9. The method of claim 6, wherein the subject was infected with severe acute respiratory syndrome coronavirus 2 (SARS COV-2).

10. The method of claim 6, wherein the first cells are human embryonic kidney cells.

11. The method of claim 10, wherein the human embryonic kidney cells are 293 cells.

12. The method of claim 6, wherein the sample is serum or plasma.

13. The method of claim 6, wherein the viral expression vector is a human immunodeficiency virus (HIV) expression vector.

14. The method of claim 6, wherein ACE-2 and TMPRSS2 are transiently expressed by the target cell.

15. The method of claim 14, wherein ACE-2, TMPRSS2, or both are stably expressed by the target cell.

16. The method of claim 6, wherein the neutralizing antibody response in the sample is correlated to a titer of total anti-coronavirus antibody as measured for the subject.

17. A method for evaluating an effect of a mutation in a spike protein on susceptibility to an anti-SARS COV-2 antibody, comprising:

(a) transfecting into a first portion of a plurality of first cells:
  i) a nucleic acid encoding a control coronavirus spike protein, and
  ii) a viral expression vector which comprises an indicator nucleic acid which produces a detectable signal;

(b) transfecting into a second portion of a plurality of first cells:
  i) a nucleic acid encoding a coronavirus spike protein that comprises a mutation; and
  ii) a viral expression vector which comprises an indicator nucleic acid which produces a detectable signal;

(c) incubating the first and second portion of first cells separately under conditions such that the first portion cells produce first viral particles comprising the control coronavirus spike protein, and the second portion cells produce second viral particles comprising the coronavirus spike protein having the mutation;

(d) contacting the first viral particles of step (c) with a first portion of the composition of claim 1 in the presence of a sample comprising an antibody that binds SARS COV-2;

(e) contacting the second viral particles of step (c) with a second portion of the composition of claim 1 in the presence of a sample comprising an antibody that binds SARS CoV-2; and (f) measuring an amount of the detectable signal produced by the target cell in steps (d) and (e), wherein a reduced amount of signal produced by the target cell in step (d) as compared to the signal produced by the target cell in step (e) indicates that the mutation in the spike protein confers a reduced susceptibility of the viral particles to the anti-SARS COV-2 antibody.

* * * * *

UNITED STATES PATENT AND TRADEMARK OFFICE
CERTIFICATE OF CORRECTION

| | | |
|---|---|---|
| PATENT NO. | : 12,366,581 B2 | Page 1 of 1 |
| APPLICATION NO. | : 17/359064 | |
| DATED | : July 22, 2025 | |
| INVENTOR(S) | : Christos J. Petropoulos, Mary T. Wrin and Danielle DiTirro | |

It is certified that error appears in the above-identified patent and that said Letters Patent is hereby corrected as shown below:

In the Claims

In Column 36, Line 61, Claim 9: please delete "COV-2" and insert --CoV-2--

In Column 37, Line 12, Claim 17: please delete "COV-2" and insert --CoV-2--

In Column 38, Line 12, Claim 17: please delete "COV-2" and insert --CoV-2--

In Column 38, Line 24, Claim 17: please delete "COV-2" and insert --CoV-2--

Signed and Sealed this
Second Day of December, 2025

John A. Squires
*Director of the United States Patent and Trademark Office*